United States Patent
Kojima et al.

(10) Patent No.: US 9,408,562 B2
(45) Date of Patent: Aug. 9, 2016

(54) PET MEDICAL CHECKUP DEVICE, PET MEDICAL CHECKUP METHOD, AND NON-TRANSITORY COMPUTER READABLE RECORDING MEDIUM STORING PROGRAM

(71) Applicant: Panasonic Intellectual Property Corporation of America, Torrance, CA (US)

(72) Inventors: Yoshihiro Kojima, Hyogo (JP); Ryuji Inoue, Osaka (JP); Toru Tanigawa, Osaka (JP)

(73) Assignee: Panasonic Intellectual Property Corporation of America, Torrance, CA (US)

( * ) Notice: Subject to any disclaimer, the term of this patent is extended or adjusted under 35 U.S.C. 154(b) by 212 days.

(21) Appl. No.: 14/254,392

(22) Filed: Apr. 16, 2014

(65) Prior Publication Data

US 2014/0316216 A1    Oct. 23, 2014

(30) Foreign Application Priority Data

Apr. 23, 2013  (JP) ................. 2013-090087

(51) Int. Cl.
*A61B 5/00* (2006.01)
*A61B 5/11* (2006.01)
*A61B 7/04* (2006.01)

(52) U.S. Cl.
CPC ............. *A61B 5/1128* (2013.01); *A61B 7/04* (2013.01); *A61B 5/7282* (2013.01); *A61B 2503/40* (2013.01)

(58) Field of Classification Search
USPC ......................................... 600/301
See application file for complete search history.

(56) References Cited

U.S. PATENT DOCUMENTS

2012/0237104 A1 * 9/2012 Fouras .................. A61B 5/08
382/132

FOREIGN PATENT DOCUMENTS

| JP | 2002-51990 | 2/2002 |
| JP | 2009-165416 | 7/2009 |
| JP | 5142038 | 2/2013 |

* cited by examiner

*Primary Examiner* — Nicole F Lavert
(74) *Attorney, Agent, or Firm* — Wenderoth, Lind & Ponack, L.L.P.

(57) ABSTRACT

A pet medical checkup device of the present disclosure includes a shooting section that shoots a moving image of a pet, a first storage section that stores the moving image of the pet shot by the shooting section, a first database that stores motion information representing a specific motion made by the pet when the pet has a disease for each disease of the pet, a first determination section that determines whether or not the pet is making the specific motion represented by the motion information stored in the first database using the moving image of the pet stored in the first storage section, and an estimation section that estimates the disease of the pet based on a determination result of the first determination section.

9 Claims, 14 Drawing Sheets

FIG. 2

| KIND OF PET | DISEASE OF PET | SPECIFIC MOTION | MOTION CHARACTERISTIC PATTERN |
|---|---|---|---|
| DOG | RHINITIS | SNEEZING | $A_1 = (a_{11}, a_{12}, \cdots, a_{1n})$ |
| | | COUGHING | $A_2 = (a_{21}, a_{22}, \cdots, a_{2n})$ |
| | | ⋮ | ⋮ |
| | DERMATITIS | SCRATCHING SKIN | $A_k = (a_{k1}, a_{k2}, \cdots, a_{kn})$ |
| | ⋮ | ⋮ | ⋮ |
| CAT | RHINITIS | SNEEZING | $B_1 = (b_{11}, b_{12}, \cdots, b_{1n})$ |
| | ⋮ | ⋮ | ⋮ |

FIG. 3

| KIND OF PET | DISEASE OF PET | NAME OF AFFECTED PART | SPECIFIC AFFECTED PART IMAGE | IMAGE CHARACTERISTIC PATTERN |
|---|---|---|---|---|
| DOG | RHINITIS | NOSE | NOSE IS RUNNING | $P_1 = (p_{11}, p_{12}, \cdots, p_{1m})$ |
| | | EYE | GUM IS IN EYE | $P_2 = (p_{21}, p_{22}, \cdots, p_{2m})$ |
| | ⋮ | ⋮ | ⋮ | ⋮ |
| | DERMATITIS | SCRATCHED SKIN | HAIR FALLS OUT AND SKIN IS RED | $P_k = (p_{k1}, p_{k2}, \cdots, p_{km})$ |
| | ⋮ | ⋮ | ⋮ | ⋮ |
| CAT | RHINITIS | NOSE | NOSE IS RUNNING | $Q_1 = (q_{11}, q_{12}, \cdots, q_{1m})$ |
| | ⋮ | ⋮ | ⋮ | ⋮ |

| KIND OF PET | DISEASE OF PET | SOUND GENERATED BY SPECIFIC MOTION | MOTION SOUND CHARACTERISTIC PATTERN |
|---|---|---|---|
| DOG | RHINITIS | SOUND OF SNEEZING | $T_1 = (t_{11}, t_{12}, \cdots, t_{1r})$ |
| | RHINITIS | SOUND OF COUGHING | $T_2 = (t_{21}, t_{22}, \cdots, t_{2r})$ |
| | ... | ... | ... |
| | DERMATITIS | SOUND OF SCRATCHING SKIN | $T_k = (t_{k1}, t_{k2}, \cdots, t_{kr})$ |
| CAT | RHINITIS | SOUND OF SNEEZING | $U_1 = (u_{11}, u_{12}, \cdots, u_{1r})$ |
| | ... | ... | ... |

53

PET MEDICAL CHECKUP DEVICE, PET MEDICAL CHECKUP METHOD, AND NON-TRANSITORY COMPUTER READABLE RECORDING MEDIUM STORING PROGRAM

TECHNICAL FIELD

The present disclosure relates to a device for checkup of the health of a pet such as a dog or a cat, a method for checkup of the health of the pet, and a non-transitory computer readable recording medium storing a program.

BACKGROUND ART

In recent years, a consciousness that a pet is not just a companion animal but a "family member" becomes common, and the pet is taken care very carefully. In addition, with the prevalence of pet food having high nutritional value and vaccine, the life span of the pet is significantly increased for the past 20 years.

On the other hand, with the increase in the life span of the pet, the number of pets suffering from diseases similar to adult diseases of human beings such as obesity and diabetes is increased. Accordingly, the medical cost for the disease and injury of the pet tends to be increased. Therefore, many owners are extremely careful with the health of the pet. As a result, there is a growing need for health support services such as nursing care and pet insurances that are popular among human beings.

Based on such a background, methods and systems for examining the health of the pet are conventionally proposed. When the pet feels sick, the pet cannot tell its owner the sickness directly. Consequently, in order to protect the health of the pet, disease prevention before the pet catches a disease and "early detection of the disease" before deterioration of the disease are extremely important. Therefore, in order to detect the disease of the pet early, a plurality of methods and systems that automatically detect the disease of the pet using biological information on the pet and images of the pet have been proposed.

For example, Japanese Patent Application Laid-open No. 2002-51990 discloses a health examination system that includes a sensor, a transmission section, and a body information management section. The sensor is brought into contact with the body of the pet, and detects body information (a pulse, a blood pressure, and a body temperature) on the pet. The transmission section transmits the detected body information from the sensor. The body information management section receives the body information. In this system, the body information management section manages the body information on the pet and performs abnormality detection of the body information on the pet, and transmits an emergency signal when the body information management section detects the abnormality.

In addition, Japanese Patent Application Laid-open No. 2009-165416 discloses a health examination system for the pet. In the health examination system, using an eye drawing section that draws the eye of the pet, the eye of the pet is drawn and the facial image of the pet is taken. Further, in the health examination system, biological data items such as the size of a pupil, the temperature of the eye, and the glossiness of a nose are extracted from the facial image of the pet. Subsequently, the health examination system determines the health condition of the pet from the extracted biological data items. Note that the eye drawing section draws the eye of the bet by giving stimuli such as, e.g., pictures, light, sound, and smell to the pet.

Further, Japanese Patent No. 5142038 discloses a pet management system. In the pet management system, the health condition of the pet is determined by comparing the image of the iris of the pet taken by a camera and the health condition of the pet inputted by its owner with a database, and the determination result is reported to the owner.

SUMMARY OF INVENTION

However, the system in each of Japanese Patent Application Laid-open No. 2002-51990, Japanese Patent Application Laid-open No. 2009-165416, and Japanese Patent No. 5142038 has required a further improvement.

In order to solve the problem, a pet medical checkup device according to an aspect of the present disclosure includes: a shooting section that shoots a moving image of a pet; a first storage section that stores the moving image of the pet shot by the shooting section; a first database that stores motion information representing a specific motion made by the pet when the pet has a disease for each disease of the pet; a first determination section that determines whether or not the pet is making the specific motion represented by the motion information stored in the first database using the moving image of the pet stored in the first storage section; and an estimation section that estimates the disease of the pet based on a determination result of the first determination section.

According to the pet medical checkup device according to the aspect, it is possible to achieve a further improvement.

BRIEF DESCRIPTION OF DRAWINGS

FIG. 2 is a view showing an example of information stored in a disease motion characteristic database according to the first embodiment;

FIG. 3 is a view showing an example of information stored in a second database according to the first embodiment;

FIG. 8 is a view showing an example of information stored in a disease motion sound characteristic database according to the third embodiment;

Figure 1:
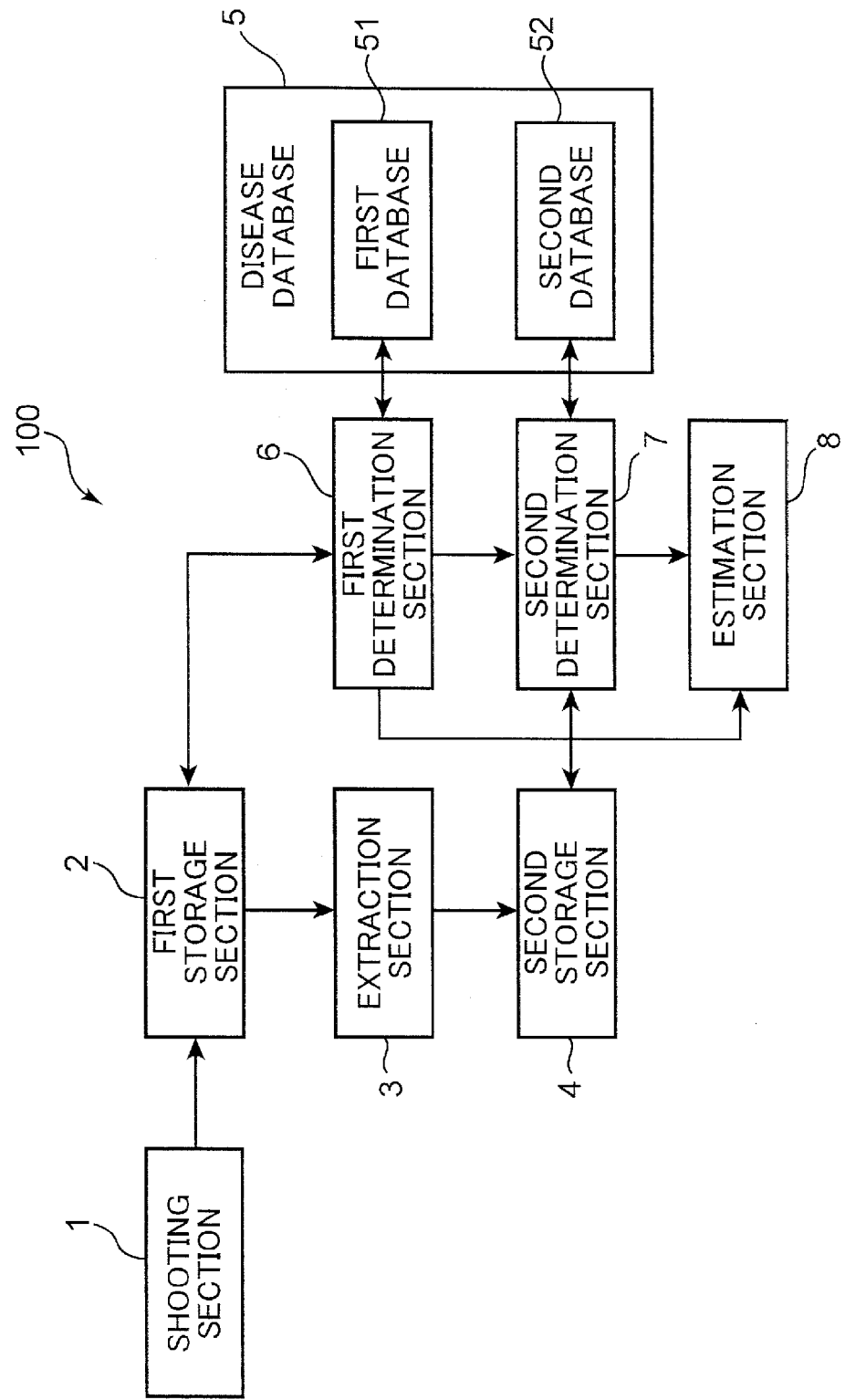
FIG. 1 is a block diagram of a pet medical checkup device according to a first embodiment.

DESCRIPTION OF EMBODIMENTS (How an Aspect of the Present Disclosure has been Invented)

First, a viewpoint of an aspect according to the present disclosure will be described.

In the system described in Japanese Patent Application Laid-open No. 2002-51990, in order to measure the body information on the pet for examining the health of the pet, it is necessary to constantly attach the sensor to the body of the pet. Therefore, the system described in Japanese Patent Application Laid-open No. 2002-51990 has a problem that stress given to the pet may be significantly great.

In the system described in Japanese Patent Application Laid-open No. 2009-165416, it is possible to acquire the information for examining the health of the pet in a non-contact manner. However, in the system described in Japanese Patent Application Laid-open No. 2009-165416, the health of the pet is determined using only the facial image. Consequently, the system described in Japanese Patent Application Laid-open No. 2009-165416 has a problem that it is not possible to detect, e.g., diseases of hands and legs of the pet, and it is difficult to improve the accuracy in the examination.

In the system described in Japanese Patent No. 5142038, the health condition of the pet is determined from medical examination interview data inputted by the owner and the iris image. Consequently, the system described in Japanese Patent No. 5142038 has a problem that it is difficult to detect the disease of the part of the body that the owner does not notice.

In view of the above studies, as shown below, the present inventors have conceived of individual aspects of the invention according to the present disclosure. An object of aspects according to the present disclosure is to provide a pet medical checkup device, a pet medical checkup method, and a program capable of detecting the disease of the pet with excellent accuracy without giving stress to the pet.

An aspect according to the present disclosure is a pet medical checkup device including a shooting section that shoots a moving image of a pet, a first storage section that stores the moving image of the pet shot by the shooting section, a first database that stores motion information representing a specific motion made by the pet when the pet has a disease for each disease of the pet, a first determination section that determines whether or not the pet is making the specific motion represented by the motion information stored in the first database using the moving image of the pet stored in the first storage section, and an estimation section that estimates the disease of the pet based on a determination result of the first determination section.

Thus, in the present aspect, the first determination section determines whether or not the pet is making the specific motion corresponding to the disease of the pet using the shot moving image of the pet. The estimation section estimates the disease of the pet based on the determination result of the first determination section. With this, it is possible to examine the health of the pet without attaching a sensor to the body of the pet. Accordingly, stress is not given to the pet. In addition, the disease is estimated from the entire motion of the pet instead of estimating the disease using only the image of a specific part such as a facial image of the pet or the like. Consequently, it is possible to examine the health of the pet with excellent accuracy.

In the aspect described above, for example, the pet medical checkup device may further include an input section for inputting a kind of the pet. The first database may store the motion information for each kind of the pet, and the first determination section may determine whether or not the pet is making the specific motion correspondingly to the kind of the pet inputted by the input section.

According to the present aspect, the first database stores the motion information for each kind of the pet, and the first determination section determines whether or not the pet is making the specific motion correspondingly to the kind of the pet inputted by the input section. Consequently, it is possible to examine the health of the pet with excellent accuracy correspondingly to the kind of the pet.

In addition, in the aspect described above, for example, the pet medical checkup device may further include an extraction section that extracts a still image of the pet from the moving image of the pet stored in the first storage section, a second storage section that stores the still image of the pet extracted by the extraction section, a second database that stores image information representing a specific affected part image of an affected part related to the disease of the pet for each disease of the pet, and a second determination section that extracts a still image of the affected part related to the disease of the pet corresponding to the specific motion from the second storage section when the first determination section determines that the pet is making the specific motion, and determines whether or not the extracted still image includes the specific affected part image represented by the image information stored in the second database. The estimation section may estimate the disease of the pet based on the determination result of the first determination section and a determination result of the second determination section.

Thus, in the present aspect, the second determination section extracts the still image of the affected part related to the disease of the pet corresponding to the specific motion from the second storage section. The second determination section determines whether or not the extracted still image includes the specific affected part image of the affected part related to the disease of the pet represented by the image information stored in the second database. Subsequently, the estimation section estimates the disease of the pet based on the determination result of the first determination section and the determination result of the second determination section. With this, the disease of the pet is estimated based on not only the motion of the pet but also the still image of the affected part of the pet related to the disease estimated from the motion. Consequently, it is possible to examine the health of the pet with higher accuracy.

In the aspect described above, for example, the pet medical checkup device may further include an input section for inputting a kind of the pet. The second database may store the image information for each kind of the pet, and the second determination section may determine whether or not the still image of the affected part of the pet includes the specific affected part image correspondingly to the kind of the pet inputted by the input section.

Thus, in the present aspect, the second database stores the image information for each kind of the pet, and the second determination section determines whether or not the still image of the affected part of the pet includes the specific affected part image correspondingly to the kind of the pet inputted by the input section. Consequently, it is possible to examine the health of the pet with excellent accuracy correspondingly to the kind of the pet.

Further, In the aspect described above, for example, the pet medical checkup device may further include a sound collection section that records a sound generated from the pet, a third storage section that stores the sound generated from the pet and recorded by the sound collection section, and a third database that stores motion sound information representing a sound generated by the specific motion made by the pet when the pet has the disease for each disease of the pet. The first determination section may determine whether or not the pet is making the specific motion represented by the motion information stored in the first database using the moving image of the pet stored in the first storage section and the motion sound information stored in the third storage section.

Thus, in the present aspect, it is determined whether or not the pet is making the specific motion represented by the motion information stored in the first database using the moving image of the pet stored in the first storage section and the motion sound information stored in the third storage section. The motion sound information stored in the third storage section represents the sound generated by the specific motion made by the pet. Consequently, even in the case where the moving image of the pet stored in the first storage section is not sharp, the first determination section can determine whether or not the pet is making the specific motion with excellent accuracy by using the motion sound information stored in the third storage section in combination.

In the aspect described above, for example, the pet medical checkup device may further include an input section for inputting a kind of the pet. The third database may store the motion sound information for each kind of the pet, and the first determination section may determine whether or not the pet is making the specific motion correspondingly to the kind of the pet inputted by the input section.

Thus, in the present aspect, the third database stores the motion sound information for each kind of the pet, and the first determination section determines whether or not the pet is making the specific motion correspondingly to the kind of the pet inputted by the input section. Consequently, it is possible to examine the health of the pet with excellent accuracy correspondingly to the kind of the pet.

In the aspect described above, for example, the pet medical checkup device may further include a shooting control section that changes a shooting condition of the shooting section. The second determination section may determine, before determining whether or not the still image extracted from the second storage section includes the specific affected part image, whether or not the still image is a determination-capable image that allows the determination, and, when determining that the still image is not the determination-capable image, the second determination section may report a detail of the determination that the still image is not the determination-capable image to the shooting control section, and the shooting control section may change the shooting condition of the shooting section based on the detail of the determination reported from the second determination section to thereby provide the still image as the determination-capable image.

Thus, in the present aspect, when the second determination section determines that the still image extracted from the second storage section is not the determination-capable image that allows the determination of whether or not the still image includes the specific affected part image, the second determination section reports the detail of the determination to the shooting control section. The shooting control section changes the shooting condition of the shooting section based on the detail of the determination reported from the second determination section to thereby provide the still image as the determination-capable image. Consequently, it becomes possible to perform the determination of whether or not the still image extracted from the second storage section includes the specific affected part image with higher accuracy.

In the aspect described above, for example, the estimation section may cause a display section to display an estimation result.

Thus, in the present aspect, the estimation result of the estimation section is displayed in the display section. Consequently, an owner of the pet can know the disease of the pet quickly with the display of the display section.

Another aspect according to the present disclosure is a pet medical checkup method in a pet medical checkup device that estimates a disease of a pet, the method including a shooting step of shooting a moving image of the pet, a storage step of causing a storage section to store the shot moving image of the pet, a preparation step of preparing a database that stores motion information representing a specific motion made by the pet when the pet has the disease for each disease of the pet, a determination step of determining whether or not the pet is making the specific motion stored in the database using the moving image of the pet stored in the storage section, and an estimation step of estimating the disease of the pet based on a determination result in the determination step.

Still another aspect according to the present disclosure is a program for controlling a pet medical checkup device that estimates a disease of a pet, the program causing a computer of the pet medical checkup device to execute a shooting step of shooting a moving image of the pet, a storage step of causing a storage section to store the shot moving image of the pet, a preparation step of preparing a database that stores motion information representing a specific motion made by the pet when the pet has the disease for each disease of the pet, a determination step of determining whether or not the pet is making the specific motion stored in the database by using the moving image of the pet stored in the storage section, and an estimation step of estimating the disease of the pet based on a determination result in the determination step.

These general or specific aspects may be implemented using a system, a method, an integrated circuit, a computer program, or a computer-readable recording medium such as a CD-ROM, or any combination of systems, methods, integrated circuits, computer programs, or recording media.

Hereinbelow, embodiments of the present disclosure will be described with reference to the drawings.

Note that each of the embodiments described below shows a general or specific example. Numerical values, shapes, materials, constituent elements, the arrangement and connection of the constituent elements, steps, and the execution order of the steps shown in the following exemplary embodiments are mere examples, and therefore do not limit the scope of the present disclosure. In addition, among the constituent elements in the following embodiments, constituent elements not recited in any one of the independent claims defining the most generic concept are described as arbitrary constituent elements.

First Embodiment

FIG. 1 is a block diagram showing the configuration of a pet medical checkup device 100 according to the present first embodiment.

As shown in FIG. 1, the pet medical checkup device 100 includes a shooting section 1, a first storage section 2, an extraction section 3, a second storage section 4, a disease database 5, a first determination section 6, a second determination section 7, and an estimation section 8.

The shooting section 1 is, e.g., a video camera, and shoots a moving image of a pet. The shooting section 1 is basically installed so as to be fixed to an arbitrary place where the pet usually lives such as a cage, a room, or a garden. The pet moves around. To cope with this, in order to reliably shoot the moving image of the pet, the shooting section 1 preferably includes a wide-angle lens that allows shooting of an entire movement range of the pet at the same time or a movable section that allows real-time tracking of the movement of the pet and shooting. However, in the case where the movement range is larger, it is necessary to install a plurality of the shooting sections 1. In addition, in order to shoot the moving image in the dark, the shooting section 1 may include a shooting function that uses infrared rays.

The first storage section 2 stores the moving image of the pet shot by the shooting section 1. The extraction section 3 extracts a still image from the moving image of the pet stored in the first storage section 2. The second storage section 4 stores the still image of the pet extracted by the extraction section 3.

In the disease database 5, the symptom of the pet is described for each kind of the pet (a dog, a cat, or the like) and each disease of the pet (rhinitis, dermatitis, or the like). The disease database 5 includes a first database 51 and a second database 52.

FIG. 2 is a view showing an example of information stored in the first database 51. As shown in FIG. 2, a specific motion as a characteristic motion frequently made by the pet when the pet has a disease is stored for each kind of the pet and each disease of the pet in the first database 51. For example, in the case where the kind of the pet is a dog and the disease is rhinitis, the specific motion of "SNEEZING" is stored. In the case where the kind of the pet is the dog and the disease is dermatitis, the specific motion of "SCRATCHING SKIN" is stored. In the case where the kind of the pet is a cat and the disease is rhinitis, the specific motion of "SNEEZING" is stored.

Note that, specifically, in the first database 51, a representative value $A_i$ of a motion pattern (hereinafter referred to as a "motion characteristic pattern") extracted from the moving image in which the pet is making the specific motion (e.g., "SNEEZING" or "SCRATCHING SKIN" of the dog) during the disease for recognizing the motion is stored. At least one representative value of the motion characteristic pattern (an example of motion information) is stored for each specific motion in the first database 51.

The representative value $A_i$ of the motion characteristic pattern is represented by the following Expression (1):

$$A_i=(a_{i1},a_{i2},\ldots,a_{in})i=1,2,\ldots,N \quad (1).$$

In Expression (1), n indicates the number of motion characteristic amounts constituting the motion characteristic pattern, and N indicates the number of representative values of the motion characteristic pattern stored in the first database 51.

Further, in the first database 51, a plurality of the specific motions may be stored for each disease. For example, in the first database 51, as shown in FIG. 2, the specific motion of "COUGHING" may be stored in addition to the specific motion of "SNEEZING" for rhinitis of the dog.

FIG. 3 is a view showing an example of information stored in the second database 52. As shown in FIG. 3, in the second database 52, the name of an affected part related to the disease of the pet and a specific affected part image as a characteristic image of the affected part during the disease are stored for each kind of the pet and each disease of the pet. For example, in the case where the kind of the pet is the dog and the disease is rhinitis, in the second database 52, "NOSE" is stored as the name of the affected part and the specific affected part image of "NOSE IS RUNNING" is stored in the image of "NOSE". In the case where the kind of the pet is the dog and the disease is dermatitis, in the second database 52, "SCRATCHED SKIN" is stored as the name of the affected part, and the specific affected part image of "HAIR FALLS OUT AND SKIN IS RED" is stored in the image of "SCRATCHED SKIN". In the case where the kind of the pet is the cat and the disease is rhinitis, in the second database 52, "NOSE" is stored as the name of the affected part, and the specific affected part image of "NOSE IS RUNNING" is stored in the image of "NOSE".

Note that, specifically, in the second database 52, a representative value $P_i$ of an image pattern (hereinafter referred to as an "image characteristic pattern") extracted from the specific affected part image as the characteristic image of the affected part when the pet has the disease (e.g., the image of "NOSE IS RUNNING" or "HAIR FALLS OUT AND SKIN IS RED" of the dog) for recognizing the specific affected part image is stored. At least one representative value of the image characteristic pattern (an example of image information) is stored for each affected part in the second database 52.

The representative value $P_i$ of the image characteristic pattern is represented by the following Expression (2):

$$P_i=(p_{i1},p_{i2},\ldots,p_{im})i=1,2,\ldots,M \quad (2).$$

In Expression (2), m indicates the number of image characteristic amounts constituting the image characteristic pattern, and M indicates the number of representative values of the image characteristic pattern stored in the second database 52.

Further, in the second database 52, a plurality of the specific affected part images may also be stored for each disease. For example, in the second database 52, as shown in FIG. 3, the specific affected part image of "GUM IS IN EYE" may be stored in addition to the specific affected part image of "NOSE IS RUNNING" for rhinitis of the dog.

The first determination section 6 determines whether or not the pet is making the specific motion during the disease stored in the first database 51 using the moving image of the pet of predetermined time (e.g., 10 seconds) stored in the first storage section 2. Note that the predetermined time may be set to time in which the determination can be performed from the moving image of the pet.

In the case where the first determination section 6 determines that the pet is making the specific motion during the disease, the second determination section 7 extracts the still image of the affected part of the pet related to the disease corresponding to the determined specific motion from the second storage section 4. The second determination section 7 determines whether or not the extracted still image includes the specific affected part image of the affected part of the pet stored in the second database 52.

The estimation section 8 estimates the disease of the pet using the determination result of the first determination section 6 and the determination result of the second determination section 7.

Figure 4:
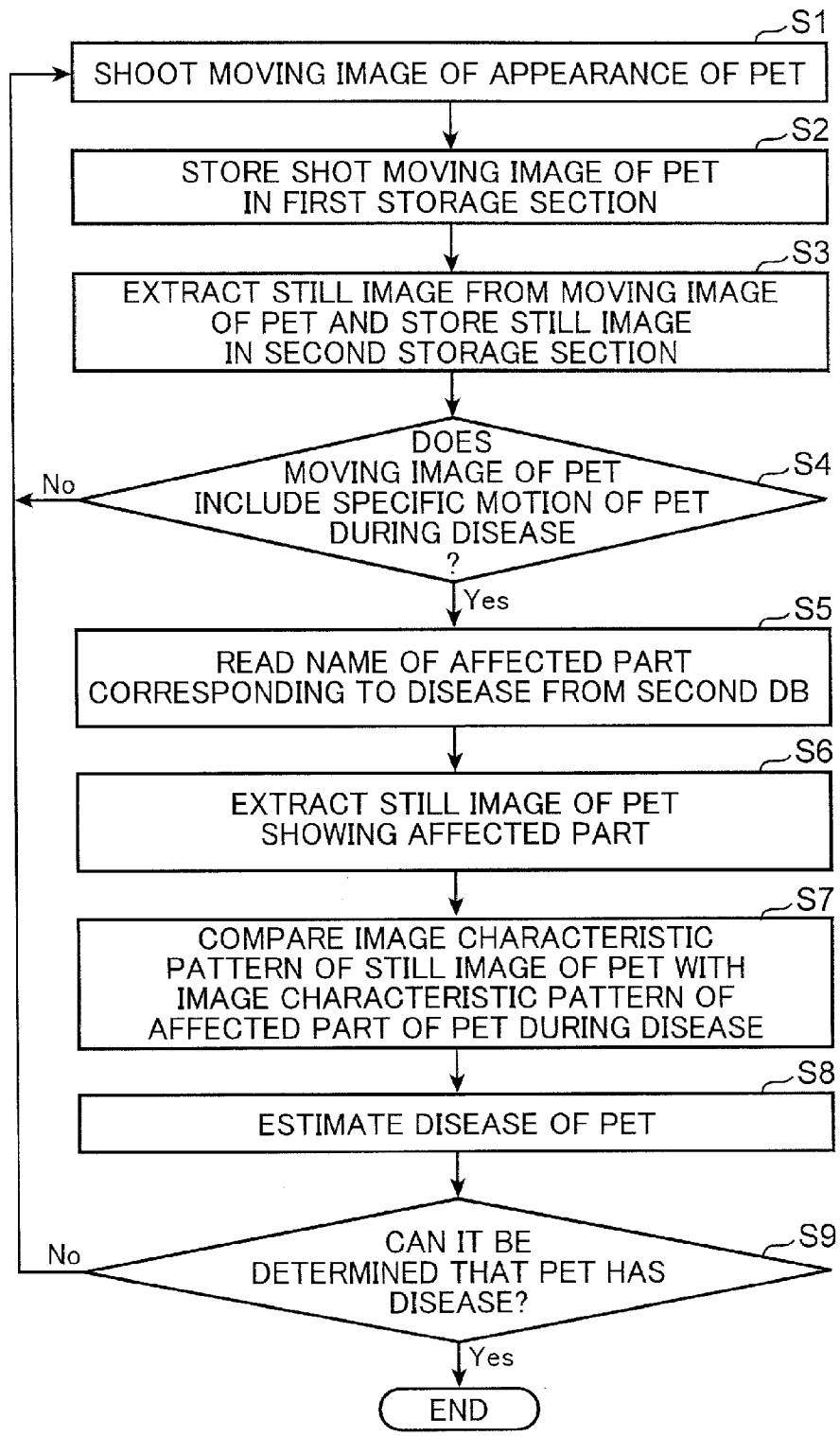
FIG. 4 is a flowchart of a pet medical checkup process by the pet medical checkup device according to the first embodiment.

FIG. 4 is a flowchart showing the flow of the process of the pet medical checkup device 100 in the present embodiment. In the present embodiment, the operation of the thus configured pet medical checkup device 100 will be described hereinbelow using FIG. 4.

First, the shooting section 1 shoots the moving image of the appearance of the pet (S1). Subsequently, the shooting section 1 stores the shot moving image in the first storage section 2 (S2). Next, the extraction section 3 extracts the still image of the pet from the moving image of the pet retained in the first storage section 2, and stores the still image in the second storage section 4 (S3).

Herein, as a method for extracting the still image from the moving image of the pet, the extraction section 3 can adopt various methods. For example, the extraction section 3 may obtain the still image from the moving image every predetermined time (e.g., 100 mm second) and store the still image in the second storage section 4. In addition, for example, the extraction section 3 may calculate an inter-frame difference in each frame of the moving image and, in the case where the calculated difference is not less than a predetermined threshold value (i.e., in the case where it is determined that the pet has moved), the extraction section 3 may store the frame in the second storage section 4.

Next, the first determination section 6 determines whether or not the pet is making the specific motion of the pet during the disease stored in the first database 51 using the moving image of the pet stored in the first storage section 2 (S4).

Specifically, the first determination section 6 extracts the motion characteristic pattern for recognizing the motion of the pet from the moving image of the pet stored in the first storage section 2. Next, the first determination section 6 compares the extracted motion characteristic pattern with all of the representative values of the motion characteristic patterns of the pet stored in the first database 51, and determines the degree of similarity of each representative value. When the degree of similarity is larger than a predetermined threshold value, the first determination section 6 determines that the pet is making the specific motion indicated by the representative value. In this case, the first determination section 6 outputs the disease corresponding to the specific motion to the second determination section 7 as a candidate for the disease of the pet.

Note that the first determination section 6 may output only the disease corresponding to the highest degree of similarity as the candidate for the disease of the pet to be outputted to the second determination section 7. Alternatively, the first determination section 6 may output a plurality of the diseases corresponding to a predetermined number of degrees of similarity that are selected in descending order to the second determination section 7 as the candidates for the disease. Further, alternatively, the first determination section 6 may also output a plurality of the diseases corresponding to the degrees of similarity that are not less than a predetermined threshold value to the second determination section 7 as the candidates for the disease.

In addition, the first determination section 6 outputs the degree of similarity of the candidate for the disease of the pet determined in the above manner to the estimation section 8 as a degree of reliability DR1 (i)(i=1, 2, . . . , L wherein L is the number of candidates for the disease) of each candidate for the disease.

For example, a motion characteristic pattern X obtained from the shot moving image of the pet is represented by the following Expression:

$$X=(x_1, x_2, \ldots, x_n) \quad (3).$$

The number of all of the representative values of the motion characteristic patterns for each disease stored in the first database 51 is represented by N. The first determination section 6 compares the motion characteristic pattern X with N representative values $A_i$ (i=1 to N) of the motion characteristic patterns for each disease, and determines the degree of similarity of each representative value. Note that the degree of similarity may be appropriately determined using known temporal pattern recognition technologies such as, e.g., dynamic programming (DP) matching and a hidden Markov model (HMM).

Herein, when the degree of similarity of the representative value $A_1$ to the motion characteristic pattern X is larger than the predetermined threshold value, the first determination section 6 determines that the pet is making the specific motion of "SNEEZING". The first determination section 6 outputs the disease "RHINITIS" as the cause of the motion to the second determination section 7 as the candidate for the disease of the pet together with the calculated degree of similarity.

On the other hand, when the degrees of similarity of all of the representative values are smaller than the predetermined threshold value, the first determination section 6 determines that it is not possible to determine that the pet has the disease from the shot moving image of the pet (No in S4), and the process flow returns to the process in S1 in which the moving image of the pet is shot.

In the case where the first determination section 6 determines that the moving image of the pet includes the specific motion of the pet during the disease (Yes in S4), the second determination section 7 performs the following processes in S5 to S7.

First, the second determination section 7 reads, from the second database 52, the affected part corresponding to each candidate for the disease of the pet outputted from the first determination section 6 (S5). Next, the second determination section 7 extracts the still image of the pet showing the read affected part from the second storage section 4 (S6). For example, when the disease of the pet is rhinitis, the second determination section 7 reads "NOSE" and "EYE" as the affected part from the second database 52 in S5.

Subsequently, in S6, the second determination section 7 extracts the still image showing "NOSE" and "EYE" of the pet from a plurality of the still images stored in the second storage section 4. Note that, as an extraction method, known common image recognition technologies used in the case where the eye and nose are extracted when the facial image of a human being is recognized may be used.

Lastly, in S7, the second determination section 7 compares the still image showing the extracted affected part with the specific affected part image of the affected part of the pet during the disease stored in the second database 52. Subsequently, the second determination section 7 determines whether or not the extracted still image includes the specific affected part image of the affected part.

Specifically, the second determination section 7 extracts the image characteristic pattern for recognizing the characteristic pattern of the image of the affected part of the pet from the still image of the pet showing the affected part of the pet. Next, the second determination section 7 compares the extracted image characteristic pattern with all of the representative values of the image characteristic patterns for each disease of the pet stored in the second database 52, and determines the degree of similarity of each representative value. Subsequently, the second determination section 7 outputs the maximum value of the determined degrees of similarity to the estimation section 8 as the degree of reliability of the candidate for the disease.

Herein, specific examples of S6 to S7 will be described. For example, in the case where the candidate for the disease is "RHINITIS", as shown in FIG. 3, the affected parts are "NOSE" and "EYE". Accordingly, the second determination section 7 firstly extracts the still image showing "NOSE" of the pet from the second storage section 4. Next, the second determination section 7 extracts an image characteristic pattern $Y_1$ from the extracted still image.

The image characteristic pattern $Y_1$ is represented by the following Expression:

$$Y_1 = (y_{11}, y_{12}, \ldots, y_{1m}) \qquad (4).$$

The second determination section 7 reads an image characteristic pattern $P_1$ representing the specific affected part image of "NOSE IS RUNNING" of the affected part "NOSE" of the disease "RHINITIS" from among the image characteristic patterns for each disease stored in the second database 52. The image characteristic pattern $P_1$ is represented by the following Expression:

$$P_1 = (p_{11}, p_{12}, \ldots, p_{1m}) \qquad (5).$$

The second determination section 7 compares the image characteristic pattern $Y_1$ of Expression (4) extracted from the still image stored in the second storage section 4 with the image characteristic pattern $P_1$ of Expression (5), and determines a degree of similarity $DS_1$. Note that the second determination section 7 may appropriately determine the degree of similarity using known image pattern recognition technologies such as, e.g., a Bayesian recognition method, subspace method, and neural network.

Next, the second determination section 7 extracts the still image showing "EYE" of the pet from the second storage section 4. Next, the second determination section 7 extracts an image characteristic pattern $Y_2$ from the extracted still image.

The image characteristic pattern $Y_2$ is represented by the following Expression:

$$Y_2 = (y_{21}, y_{22}, \ldots, y_{2m}) \qquad (6).$$

The second determination section 7 reads an image characteristic pattern $P_2$ representing the specific affected part image of "GUM IS IN EYE" of the affected part "EYE" of the disease "RHINITIS" from among the image characteristic patterns for each disease stored in the second database 52. The image characteristic pattern $P_2$ is represented by the following Expression:

$$P_2 = (P_{21}, p_{22}, \ldots, p_{2m}) \qquad (7).$$

The second determination section 7 compares the image characteristic pattern $Y_2$ of Expression (6) extracted from the still image stored in the second storage section 4 with the image characteristic pattern $P_2$ of Expression (7), and determines a degree of similarity $DS_2$.

Subsequently, the second determination section 7 outputs the larger one of the determined degrees of similarity $DS_1$ and $DS_2$ as a degree of reliability DR2 (i)(i=1, 2, ..., L wherein L is the number of candidates for the disease) to the disease "RHINITIS" to the estimation section 8.

Subsequently to S7, the estimation section 8 estimates the disease of the pet using the determination result of the first determination section 6 and the determination result of the second determination section 7 (S8). Specifically, the estimation section 8 calculates a degree of integrated reliability of each candidate for the disease IR (i)(i=1, 2, ..., L wherein L is the number of candidates for the disease) using the degree of reliability of each candidate for the disease DR1 (i)(i=1, 2, ..., L wherein L is the number of candidates for the disease) obtained from the first determination section 6 and the degree of reliability of each candidate for the disease DR2 (i)(i=1, 2, ..., L wherein L is the number of candidates for the disease) obtained from the second determination section 7 with the following Expression:

$$IR(i) = DR1(i) \times DR2(i) \qquad (8).$$

Subsequently, the estimation section 8 determines a maximum degree of integrated reliability IRmax among the degrees of integrated reliability IR (i). Note that the larger one of the degree of reliability DR1 (i) and the degree of reliability DR2 (i) may be determined as the degree of integrated reliability IR (i) instead of using Expression (8).

Lastly, the estimation section 8 determines whether or not the maximum degree of integrated reliability IRmax is larger than a predetermined threshold value (S9). In the case where the maximum degree of integrated reliability IRmax is larger than the threshold value (Yes in S9), the estimation section 8 determines the disease corresponding to the maximum degree of integrated reliability IRmax as the estimation result. On the other hand, in the case where the maximum degree of integrated reliability IRmax is smaller than the threshold value (No in S9), the estimation section 8 determines that it is not possible to determine that the pet has the disease from the shot moving image and still image of the pet, and the process flow returns to the process (S1) of shooting the moving image of the pet.

As described thus far, in the pet medical checkup device 100 according to the first embodiment, the first determination section 6 determines whether or not the pet is making the specific motion related to the disease of the pet from the shot moving image of the pet. Subsequently, the second determination section 7 extracts the still image of the affected part of the pet related to the disease of the pet as the cause of the specific motion from the second storage section 4. Further, the second determination section 7 determines whether or not the extracted still image includes the specific affected part image of the affected part of the disease of the pet stored in the second database 52. Then, the estimation section 8 estimates the disease of the pet using the determination result of the first determination section 6 and the determination result of the second determination section 7.

With this, according to the first embodiment, it is possible to examine the health condition of the pet without attaching a sensor to the body of the pet. Consequently, stress is not given to the pet. In addition, unlike Japanese Patent Application Laid-open No. 2009-165416, the disease is not estimated using only the photograph of the specific part such as the facial image of the pet or the like, but the disease of the pet is estimated based on the motion of the pet and the still image of the affected part of the pet related to the disease considered as the cause of the motion. Consequently, as compared with the system described in Japanese Patent Application Laid-open No. 2009-165416, it is possible to examine the health of the pet with excellent accuracy.

Although the pet medical checkup device 100 according to the first embodiment has been described thus far, the present disclosure is not limited to the embodiment.

For example, in the first embodiment, the estimation section 8 identifies the disease of the pet using the specific motion related to the disease of the pet extracted from the moving image of the pet and the still image of the affected part of the pet related to the disease of the pet as the cause of the specific motion. However, the present disclosure is not limited thereto.

For example, the estimation section 8 may also estimate the disease of the pet using only the determination result of the first determination section 6, i.e., the result of the determination of whether or not the moving image of the pet includes the specific motion of the pet during the disease. In the case of this modified embodiment, in the configuration of the first embodiment, the extraction section 3, the second storage section 4, the second database 52, and the second determination section 7 may be omitted.

In this case, the estimation section 8 determines the disease corresponding to the maximum value of the degree of reliability of each candidate for the disease DR1 (i)(i=1, 2, ..., L wherein L is the number of candidates for the disease) obtained from the first determination section 6 as the estimation result. In the modified embodiment, the still image of the affected part of the pet is not used in the disease examination of the pet. As a result, in the modified embodiment, the accuracy in the disease examination is low as compared with the first embodiment. However, according to the modified embodiment, it is possible to reduce process time required for the examination as compared with the first embodiment.

In addition, the first determination section 6 of the first embodiment may recognize the kind of the pet based on the moving image of the pet stored in the first storage section 2. In this case, the second determination section 7 may receive the recognition result of the first determination section 6 regarding the kind of the pet from the first determination section 6. Further, alternatively, the second determination section 7 of the first embodiment may recognize the kind of the pet based on the still image of the pet stored in the second storage section 4. In this case, the first determination section 6 may receive the recognition result of the second determination section 7 regarding the kind of the pet from the second determination section 7. In these cases, the first determination section 6 and the second determination section 7 are capable of reading data corresponding to the kind of the pet with higher accuracy from the first database 51 and the second database 52.

Additionally, in the first embodiment, data is stored for each kind of the pet in each of the first database 51 and the second database 52. However, the present disclosure is not limited thereto. For example, the average motion pattern of the pet may be stored in the first database 51. The average image pattern of the pet may be stored in the second database 52. However, since the disease can be estimated with excellent accuracy, the first embodiment that stores the data for each kind of the pet is preferable.

Second Embodiment

In the present embodiment, a modification of the pet medical checkup device 100 according to the first embodiment will be described.

Figure 5:
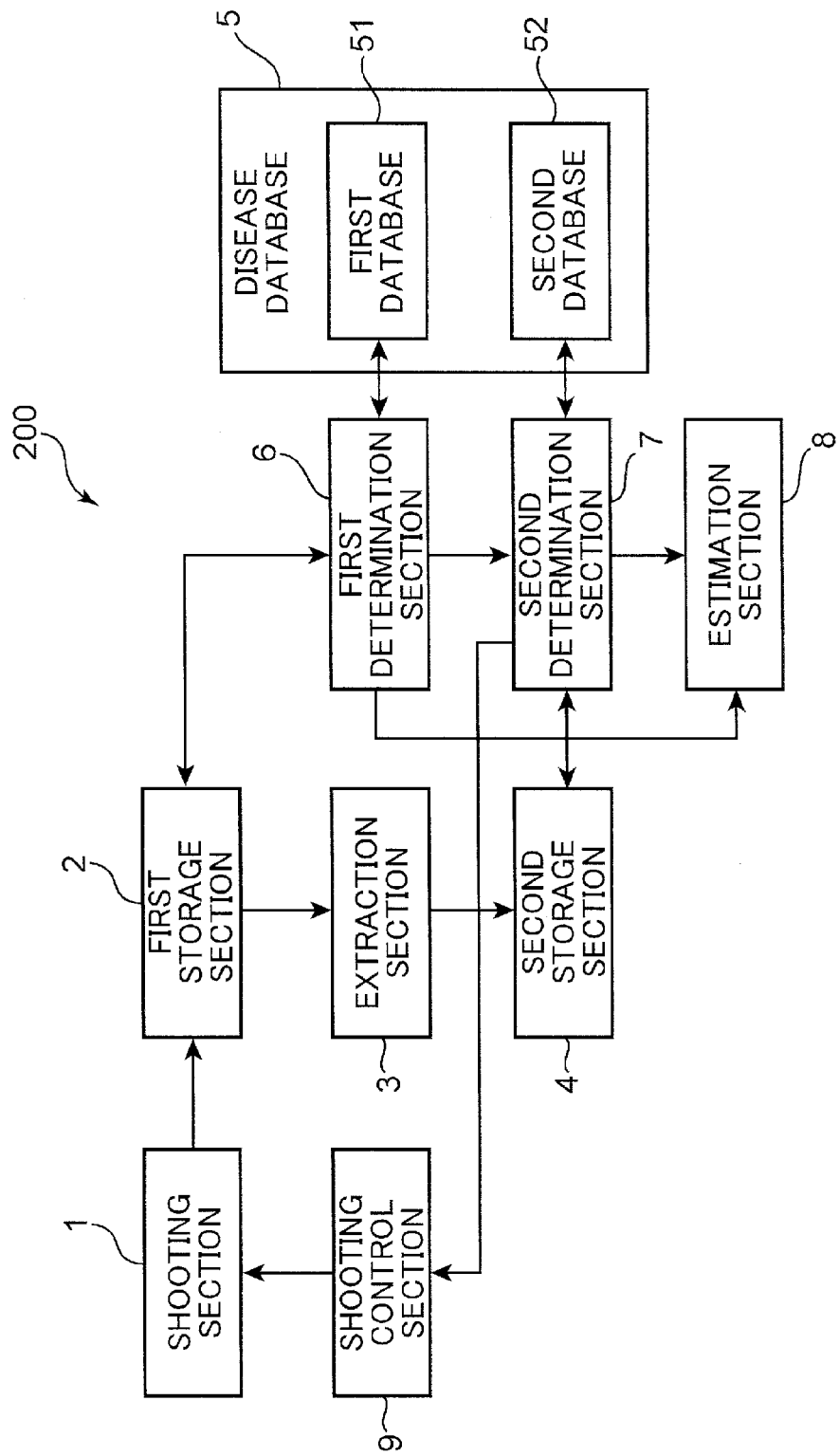
FIG. 5 is a block diagram of a pet medical checkup device according to a second embodiment.

FIG. 5 is a block diagram showing the configuration of a pet medical checkup device 200 according to the present second embodiment.

The pet medical checkup device 200 of the second embodiment has the configuration substantially similar to that of the pet medical checkup device 100 of the first embodiment. The pet medical checkup device 200 of the second embodiment is different from the pet medical checkup device 100 of the first embodiment only in that a shooting control section 9 is further provided. Accordingly, in the pet medical checkup device 200 of the second embodiment, constituent elements common to the pet medical checkup device 100 of the first embodiment are designated by the same reference numerals as those of the first embodiment.

Hereinbelow, the configuration different from that of the first embodiment will be mainly described and the detailed description of the configuration common to the first embodiment will be omitted.

The second determination section 7 of the second embodiment basically performs the operation substantially similar to that of the second determination section 7 of the first embodiment. That is, in the case where the first determination section 6 determines that the pet is making the specific motion during the disease, the second determination section 7 extracts the still image of the affected part of the pet related to the disease as the cause of the determined specific motion from the second storage section 4. The second determination section 7 determines whether or not the extracted still image includes the specific affected part image of the affected part of the pet stored in the second database 52.

However, the second determination section 7 of the second embodiment has the following function in addition to the function of the second determination section 7 in the first embodiment. The second determination section 7 of the second embodiment determines, in advance, before determining whether or not the still image of the pet extracted from the second storage section 4 includes the specific affected part image, whether or not the still image is a determination-capable image that allows the determination. In the case where the second determination section 7 of the second embodiment determines that the still image is not the determination-capable image, the second determination section 7 reports the detail of the determination to the shooting control section 9.

The second determination section 7 determines whether or not the still image extracted from the second storage section 4 is the determination-capable image that allows the determination using, e.g., the following determination criterion. For example, when the size of the affected part included in the still image is within a predetermined range (e.g., 25 to 100% of a display screen), the second determination section 7 may determine that the still image is the determination-capable image. Alternatively, when the affected part included in the still image is not blurred but sharp, the second determination section 7 may determine that the still image is the determination-capable image.

The shooting control section 9 controls the shooting section 1 based on the detail of the determination reported from the second determination section 7. Specifically, the shooting control section 9 changes shooting conditions (a zoom ratio, an aperture value, a shutter speed, and an ISO speed) of the shooting section 1 such that the second determination section 7 can recognize the still image of the affected part of the pet easily with higher accuracy.

Figure 6:
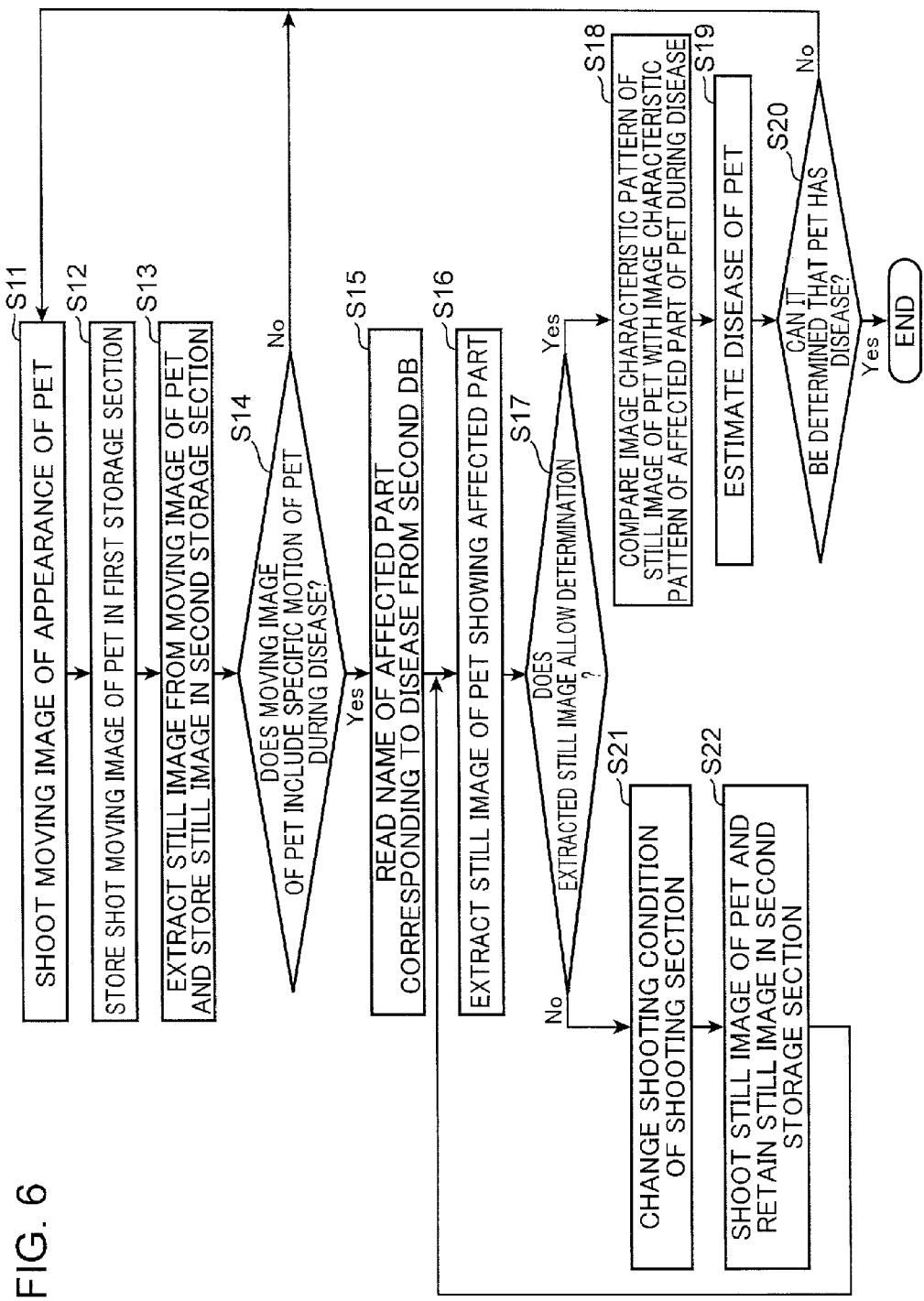
FIG. 6 is a flowchart of a pet medical checkup process by the pet medical checkup device according to the second embodiment.

FIG. 6 is a flowchart showing the flow of the process of the pet medical checkup device 200 in the present second embodiment.

In the present embodiment, the operation of the thus configured pet medical checkup device 200 will be described using FIG. 6. Note that, hereinbelow, points different from the first embodiment will be mainly described and the repeated description will be omitted. Specifically, in FIG. 6, processes from S11 to S16 are the same as the processes from S1 to S6 in the flowchart (FIG. 4) of the first embodiment. In addition, processes from S18 to S20 in FIG. 6 are the same as the processes from S7 to S9 in the flowchart (FIG. 4) of the first embodiment. Accordingly, the detailed description of the processes will be omitted and newly added processes in S17, S21, and S22 will be described in detail.

First, the process in S17 in the second determination section 7 will be described. Subsequently to the process in S16, the process in S17 is executed.

In the present embodiment, in S17, the second determination section 7 determines whether or not the still image showing the affected part of the candidate for the disease of the pet extracted from the second storage section 4 is the determination-capable image that allows the determination of whether or not the still image includes the specific affected part image of the affected part. At this point, in the case where it is determined that the still image is the determination-capable image (Yes in S17), the determination process similar to that of the first embodiment is performed (S18). Conversely, in the case where it is determined that the still image is not the determination-capable image (No in S17), the second determination section 7 reports the detail of the determination to the shooting control section 9, and the process flow advances to S21.

In S21, the shooting control section 9 changes the shooting conditions of the shooting section 1 based on the detail of the determination regarding the still image of the affected part of the pet reported from the second determination section 7, and allows the shooting section 1 to shoot the still image that allows the second determination section 7 to determine whether or not the still image includes the specific affected part image.

For example, in the case where the detail of the determination regarding the still image of the affected part indicates that "the image showing the affected part is smaller than a predetermined size", the shooting control section 9 increases the zoom ratio of the shooting section 1. In addition, in the case where the detail of the determination regarding the still image of the affected part indicates that "the image is blurred and is not sharp", the shooting control section 9 increases the shutter speed of the shooting section 1. Subsequently, the shooting control section 9 outputs the shooting conditions changed in this manner to the shooting section 1.

In S22 subsequent to S21, the shooting section 1 shoots the still image of the affected part of the pet based on the shooting conditions outputted from the shooting control section 9, and stores the still image in the second storage section 4. Subsequently, the second determination section 7 performs the processes in and subsequent to S16 again using the still image newly stored in the second storage section 4.

As described thus far, in the pet medical checkup device 200 according to the second embodiment, in the case where the image of the affected part is extremely small or in the case where the image of the affected part is blurred and is not sharp when the image of the affected part of the disease of the pet is determined, the shooting control section 9 changes the shooting conditions of the shooting section 1 based on the detail of the determination of the second determination section 7. With this, the shooting section 1 shoots the still image that allows the determination by the second determination section 7 again. With this, according to the second embodiment, it is possible to improve the determination accuracy of the second determination section 7 as compared with the first embodiment. With the improvement, it is also possible to improve the accuracy in the disease estimation by the estimation section 8.

Third Embodiment

In the present embodiment, a modification of the pet medical checkup device 100 according to the first embodiment will be described.

Figure 7:
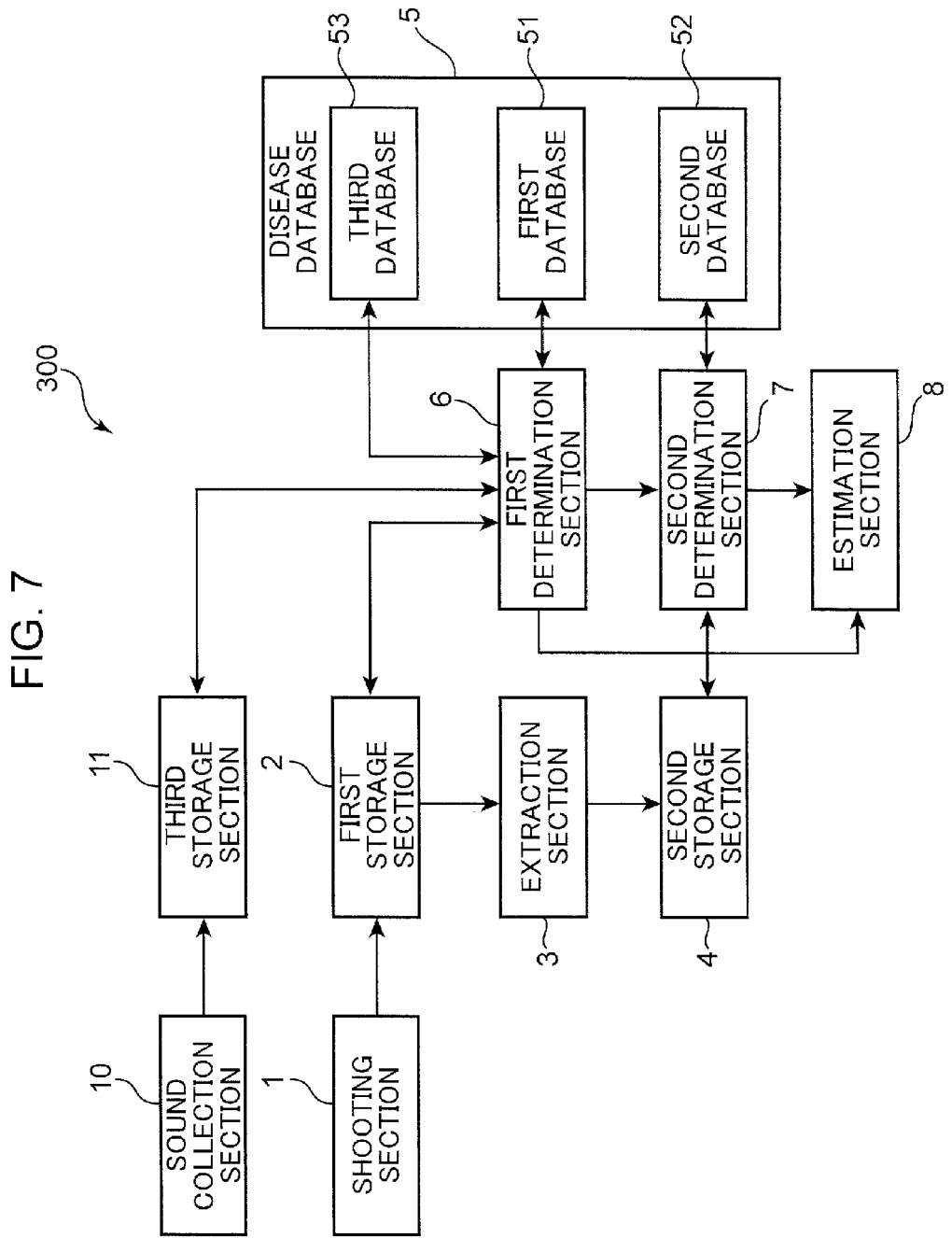
FIG. 7 is a block diagram of a pet medical checkup device according to a third embodiment.

FIG. 7 is a block diagram showing the configuration of a pet medical checkup device 300 according to the present third embodiment.

The pet medical checkup device 300 of the third embodiment has the configuration substantially similar to that of the pet medical checkup device 100 of the first embodiment. The pet medical checkup device 300 of the third embodiment is different from the pet medical checkup device 100 of the first embodiment only in that a sound collection section 10, a third storage section 11, and a third database 53 are further provided. Accordingly, in the pet medical checkup device 300 of the third embodiment, constituent elements common to the pet medical checkup device 100 of the first embodiment are designated by the same reference numerals as those of the first embodiment.

Hereinbelow, the configuration different from that of the first embodiment will be mainly described and the detailed description of the configuration common to the first embodiment will be omitted.

The sound collection section 10 is, e.g., a microphone, and records a sound generated from the pet. The sound generated from the pet is assumed to include not only the cry of the pet but also a sound generated by the motion of the pet such as, e.g., a sound generated by sneezing or a sound generated by scratching a body.

Similarly to the shooting section 1, the sound collection section 10 is installed so as to be fixed to an arbitrary place where the pet usually lives such as a case, a room, or a garden. However, since the pet moves around, in order to reliably record the sound generated from the pet, it is preferable to dispose a plurality of the sound collection sections 10.

The third storage section 11 stores the sound generated from the pet and recorded by the sound collection section 10. In the disease database 5, the symptom of the pet is described for each kind of the pet (the dog, the cat, or the like) and each disease of the pet (rhinitis, dermatitis, or the like). The disease database 5 of the third embodiment includes the third database 53 in addition to the first database 51 and the second database 52 of the first embodiment.

FIG. 8 is a view showing an example of information stored in the third database 53. As shown in FIG. 8, in the third database 53, the sound generated by the specific motion frequently made by the pet when the pet has the disease is stored for each kind of the pet and each disease of the pet. For example, in the case where the kind of the pet is the dog and the disease is rhinitis, the sound generated by the specific motion of "SNEEZING" is stored in the third database 53. In the case where the kind of the pet is the dog and the disease is dermatitis, the sound generated by the specific motion of "SCRATCHING SKIN" is stored in the third database 53. In the case where the kind of the pet is the cat and the disease is rhinitis, the sound generated by the specific motion of "SNEEZING" is stored in the third database 53.

Note that, specifically, from a moving image with sound in which the pet is making the specific motion (e.g., "SNEEZING" or "SCRATCHING SKIN" of the dog) during the disease, a motion sound generated by the motion is obtained, and a representative value $T_i$ of a motion sound pattern (hereinafter referred to as a "motion sound characteristic pattern") extracted for recognizing the motion sound is stored in the third database 53. Note that at least one representative value of the motion sound characteristic pattern (an example of motion sound information) is stored for each specific motion in the third database 53.

The representative value $T_i$ of the motion sound characteristic pattern is represented by the following Expression:

$$T_i=(t_{i1},t_{i2},\ldots,t_{ir}) i=1,2,\ldots,K \qquad (9).$$

In Expression (9), r indicates the number of motion sound characteristic amounts constituting the motion sound characteristic pattern, and K indicates the number of representative values of the motion sound characteristic pattern stored in the third database 53.

Further, in the third database 53, the motion sounds generated by a plurality of the specific motions may also be stored for each disease. For example, in the third database 53, as shown in FIG. 8, the motion sound generated by the specific motion of "COUGHING" may be stored for rhinitis of the dog in addition to the motion sound generated by the specific motion of "SNEEZING".

The first determination section 6 determines whether or not the pet is making the specific motion during the disease stored in the first database 51 using the moving image of the pet of predetermined time (e.g., ten seconds) stored in the first storage section 2 and the motion sound generated from the pet of predetermined time (e.g., one minute) stored in the third storage section 11. Note that each predetermined time may be appropriately set to time in which the determination can be performed.

Figure 9A:
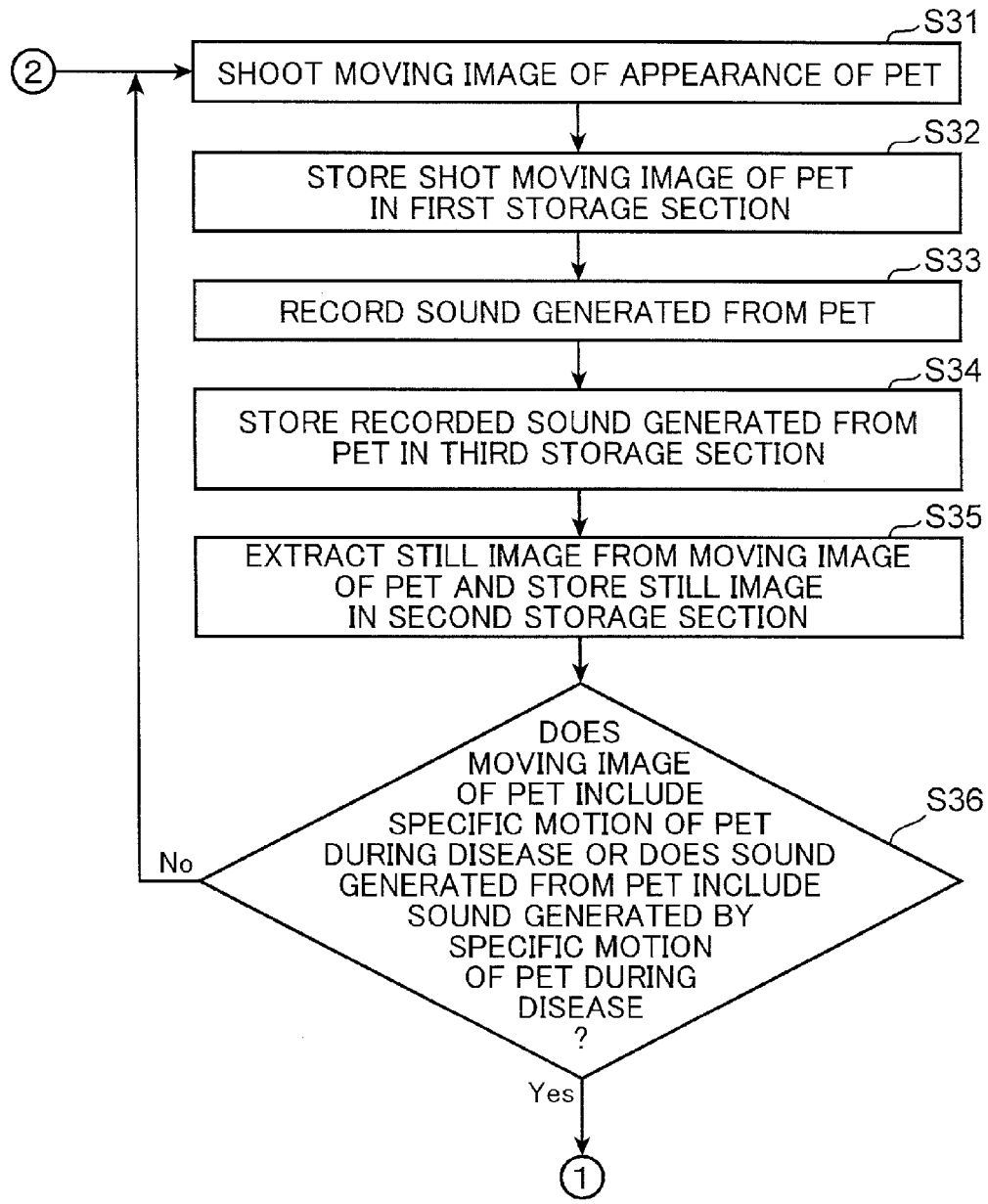
FIG. 9A is a flowchart of a pet medical checkup process by the pet medical checkup device according to the third embodiment.
Figure 9B:
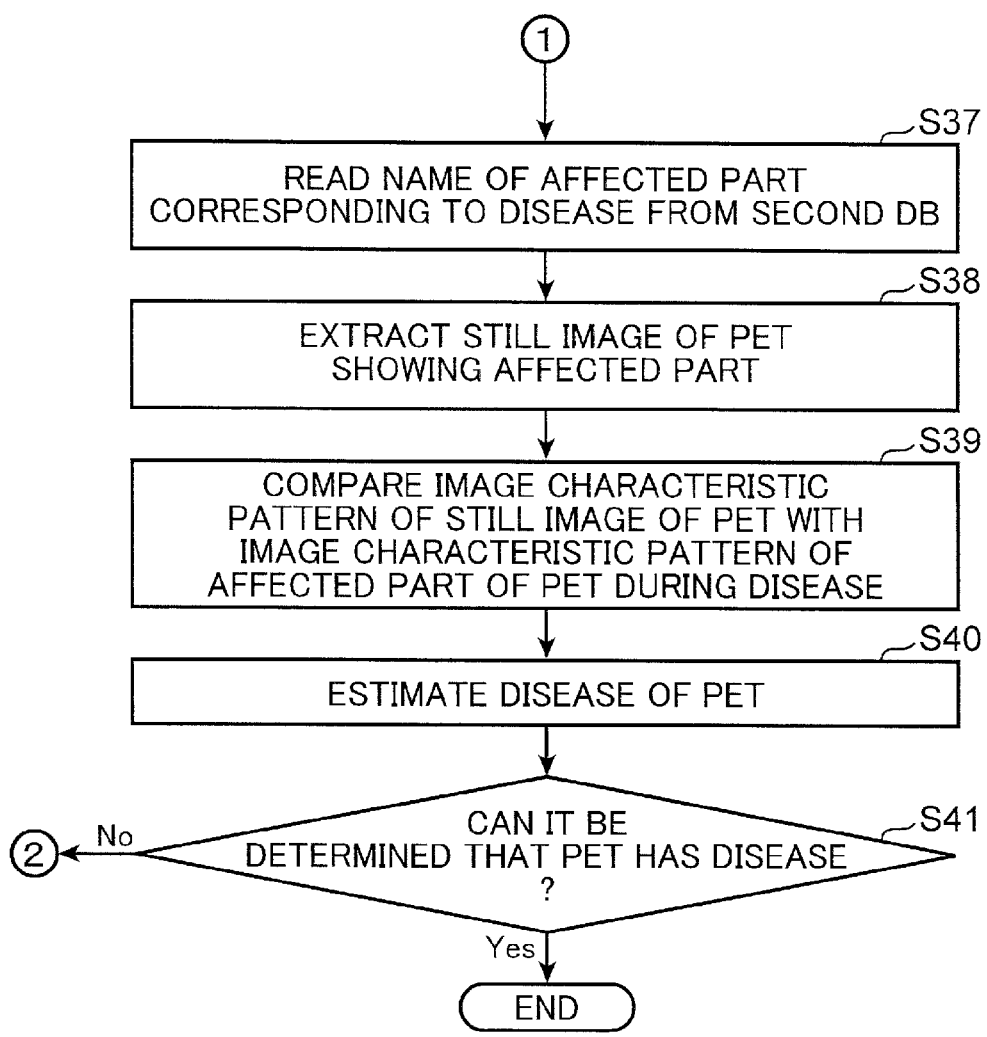
FIG. 9B is a flowchart of the pet medical checkup process by the pet medical checkup device according to the third embodiment.

Each of FIGS. 9A and 9B is a flowchart showing the flow of the process of the pet medical checkup device 300 in the present third embodiment.

In the present embodiment, the operation of the thus configured pet medical checkup device 300 will be described hereinbelow using FIGS. 9A and 9B. Note that, hereinbelow, points different from the first embodiment will be mainly described and the repeated description will be omitted. Specifically, in FIGS. 9A and 9B, processes from S37 to S41 are the same as the processes from S5 to S9 in the flowchart (FIG. 4) of the first embodiment. Accordingly, the description of the processes will be omitted, and processes from S31 to S36, mainly newly added processes in S33, S34, and S36 will be described in detail.

Similarly to the first embodiment, first, the shooting section 1 shoots the moving image of the appearance of the pet (S31). Subsequently, the shooting section 1 stores the shot moving image in the first storage section 2 (S2).

In addition, at the same time as the shooting by the shooting section 1, the sound collection section 10 records the sound generated from the pet (S33). Subsequently, the sound collection section 10 stores the recorded sound in the third storage section 11 (S34). Note that the recording by the sound collection section 10 may be started before the shooting of the moving image by the shooting section 1.

Next, similarly to the first embodiment, the extraction section 3 extracts the still image of the pet from the moving image of the pet retained in the first storage section 2, and stores the still image in the second storage section 4 (S35).

Subsequently, the first determination section 6 determines whether or not the pet is making the specific motion of the pet during the disease stored in the first database 51 using the moving image of the pet stored in the first storage section 2 and the motion sound generated from the pet stored in the third storage section 11 (S36).

Specifically, the first determination section 6 extracts the motion characteristic pattern for recognizing the motion of the pet from the moving image of the pet stored in the first storage section 2. Next, the first determination section 6 compares the extracted motion characteristic pattern with all of the representative values of the motion characteristic patterns of the pet stored in the first database 51, and determines the degree of similarity of each representative value. When the degree of similarity is larger than the predetermined threshold value, the first determination section 6 determines that the pet is making the specific motion indicated by the representative value. In this case, the first determination section 6 determines the disease corresponding to the specific motion as a first candidate group of the disease of the pet. Note that a specific method for determining the degree of similarity is assumed to be based on the method described in the first embodiment.

In addition, the first determination section 6 extracts the motion sound characteristic pattern for recognizing the motion sound of the pet from the motion sound generated from the pet stored in the third storage section 11. Next, the first determination section 6 compares the extracted motion sound characteristic pattern with all of the representative values of the motion sound characteristic patterns of the pet stored in the third database 53, and determines the degree of similarity of each representative value. When the degree of similarity is larger than a predetermined threshold value, the first determination section 6 determines that the pet is making the specific motion indicated by the representative value. In this case, the first determination section 6 determines the disease corresponding to the specific motion as a second candidate group of the disease of the pet.

Hereinbelow, a process of determining the candidate for the disease of the pet from the motion sound generated from the pet will be specifically described.

For example, a motion sound characteristic pattern Z generated from the pet is represented by the following Expression:

$$Z = (z_1, z_2, \ldots, z_r) \tag{10}$$

The number of all of the representative values of the motion sound characteristic patterns for each disease stored in the third database 53 is represented by K. The first determination section 6 compares the motion sound characteristic pattern Z with K representative values $T_i$ (i=1 to K) of the motion sound characteristic patterns for each disease, and determines the degree of similarity of each representative value. Note that the degree of similarity may be determined using known temporal pattern recognition technologies such as, e.g., DP matching and the hidden Markov model (HMM).

At this point, if the degree of similarity of the representative value $T_i$ to the motion sound characteristic pattern Z is larger than the predetermined threshold value, the first determination section 6 determines that the pet is making the specific motion of "SNEEZING". The first determination section 6 determines "RHINITIS" as the disease as the cause of the motion as the second candidate group of the disease of the pet.

Note that the first determination section 6 may output only the disease corresponding to the maximum degree of similarity of the characteristic pattern as each of the first and second candidate groups of the disease of the pet to be outputted to the second determination section 7. Alternatively, the first determination section 6 may output a plurality of the diseases corresponding to a predetermined number of degrees of similarity that are selected in descending order to the second determination section 7. Further, alternatively, the first determination section 6 may also output a plurality of the diseases corresponding to the degrees of similarity that are not less than a predetermined threshold value to the second determination section 7. Similarly to the first embodiment, the degree of similarity of the candidate for the disease of the pet determined in this manner is determined as a degree of reliability DR3 (i)(i=1, 2, . . . , L wherein L is the number of candidates for the disease) of the candidate for the disease.

Lastly, the first determination section 6 outputs the combination of the first candidate group of the disease of the pet determined from the moving image of the pet and the second candidate group of the disease of the pet determined from the motion sound generated from the pet to the second determination section 7 and the estimation section 8 together with the calculated degrees of reliability as the candidates for the disease of the pet.

Thus, in the case where the first determination section 6 determines that the pet is making the specific motion of the pet during the disease (Yes in S36), the second determination section 7 performs the subsequent processes in S37 to S41.

On the other hand, in the case where the first and second candidates for the disease of the pet are not present, i.e., in the case where all of the degrees of similarity of the characteristic patterns are smaller than the predetermined threshold value, the first determination section 6 determines that it is not possible to determine that the pet has the disease from the shot moving image of the pet and the motion sound (No in S36), and the process flow returns to the process in S31 in which the moving image of the pet is shot.

As described thus far, in the pet medical checkup device 300 according to the third embodiment, the first determination section 6 determines whether or not the pet is making the specific motion related to the disease of the pet using the motion sound generated from the pet and recorded by the sound collection section 10 in addition to the moving image of the pet shot by the shooting section 1. When the shooting section 1 is used, there are cases where the shot moving image is not sharp due to poor shooting conditions or only a part of the body of the pet is shown in the shot moving image because the pet has moved out of an imaging field. Even in such cases, according to the third embodiment, it is possible to determine that the pet is making the specific motion related to the disease of the pet. Consequently, according to the third embodiment, it is possible to improve the determination accuracy of the first determination section 6 as compared with the first embodiment. In addition, with the improvement, it is also possible to improve the accuracy in the estimation of the disease in the estimation section 8.

Note that, in the present third embodiment, the description has been given based on the configuration obtained by adding the sound collection section 10, the third storage section 11, and the third database 53 to the configuration of the first embodiment. Alternatively, the third embodiment may have the configuration obtained by adding the sound collection section 10, the third storage section 11, and the third database 53 to the configuration of the second embodiment.

Fourth Embodiment

In the present embodiment, a modification of the pet medical checkup device 100 according to the first embodiment will be described.

Figure 10:
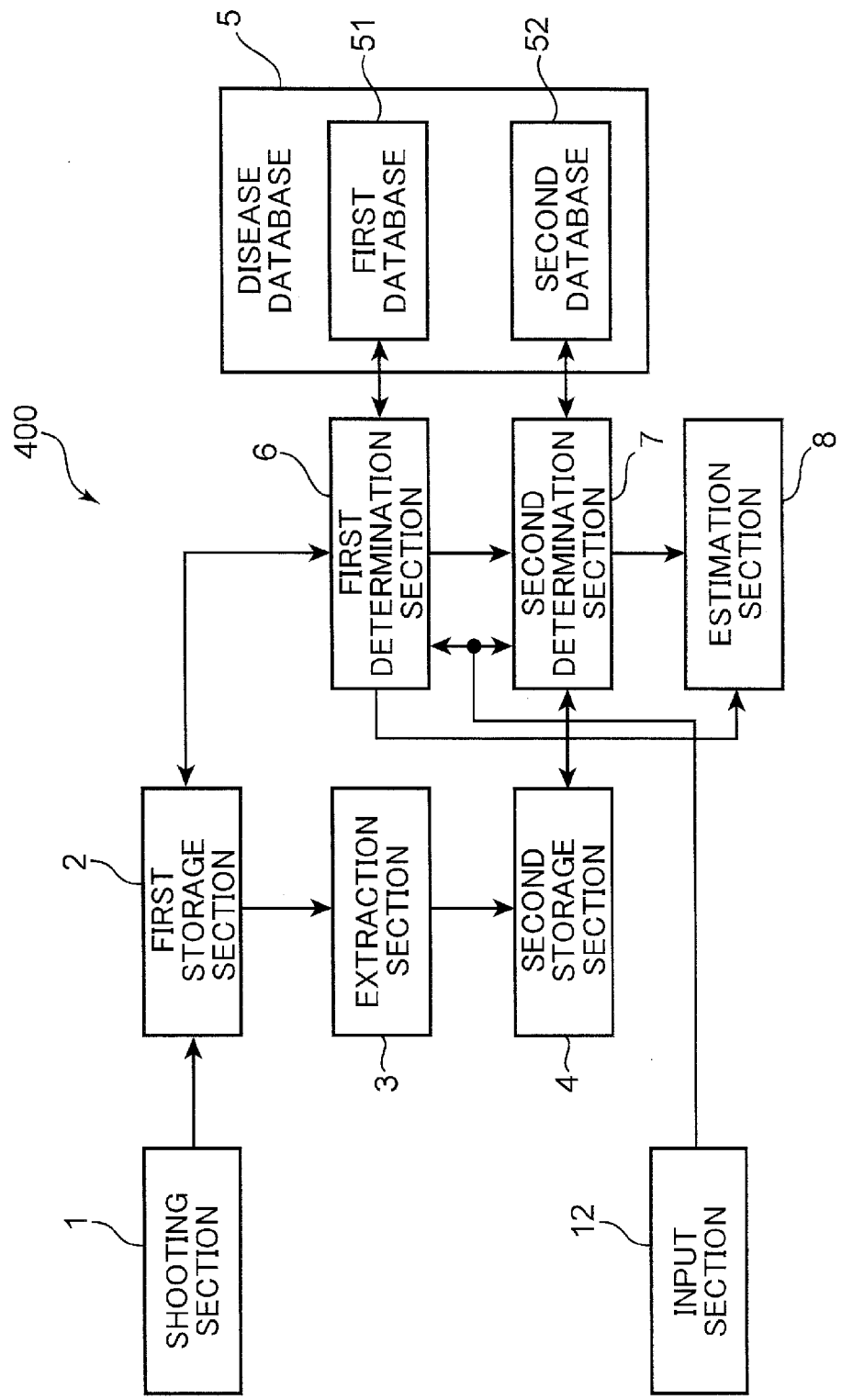
FIG. 10 is a block diagram of a pet medical checkup device according to a fourth embodiment.

FIG. 10 is a block diagram showing the configuration of a pet medical checkup device 400 according to the present fourth embodiment.

The pet medical checkup device 400 of the fourth embodiment has the configuration substantially similar to that of the pet medical checkup device 100 of the first embodiment. The pet medical checkup device 400 of the fourth embodiment is different from the pet medical checkup device 100 of the first embodiment only in that an input section 12 is further provided. Accordingly, in the pet medical checkup device 400 of the fourth embodiment, constituent elements common to the pet medical checkup device 100 of the first embodiment are designated by the same reference numerals as those of the first embodiment. Hereinbelow, the configuration different from that of the first embodiment will be mainly described and the detailed description of the configuration common to the first embodiment will be omitted.

The input section 12 is used by a user for inputting the kind of the pet. The input section 12 may be, e.g., a mobile terminal having a touch panel such as a so-called smartphone or tablet. The input section 12 may also be, e.g., a keyboard of a personal computer.

The first determination section 6 reads data corresponding to the kind of the bet inputted through the input section 12 from the first database 51, and performs the determination. The second determination section 7 reads the data corresponding to the kind of the pet inputted through the input section 12 from the second database 52, and performs the determination.

As described thus far, in the pet medical checkup device 400 according to the fourth embodiment, the first determination section 6 and the second determination section 7 read the data corresponding to the kind of the pet inputted through the input section 12 by the user from the first database 51 and the second database 52. Consequently, according to the fourth embodiment, it is possible to read the data corresponding to the pet with higher accuracy. As a result, each of the first determination section 6 and the second determination section 7 can perform the determination more accurately. With this, it is also possible to improve the accuracy in the estimation of the disease in the estimation section 8.

Note that, in the fourth embodiment, the description has been given based on the configuration obtained by adding the input section 12 to the configuration of the first embodiment. Alternatively, the fourth embodiment may also have the configuration obtained by adding the input section 12 to the configuration of the second or third embodiment.

Fifth Embodiment

In the present embodiment, a modification of the pet medical checkup device 100 according to the first embodiment will be described.

Figure 11:
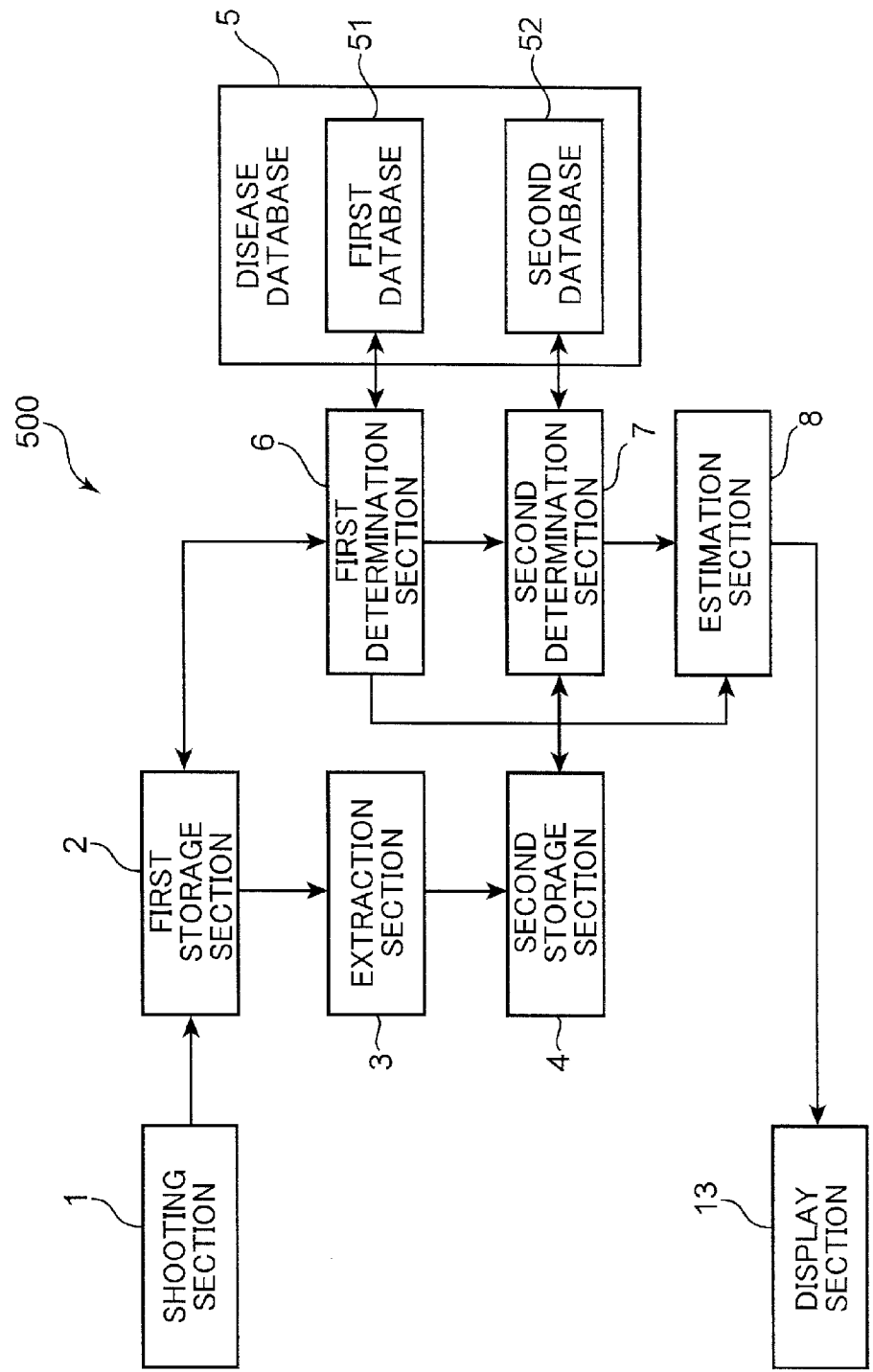
FIG. 11 is a block diagram of a pet medical checkup device according to a fifth embodiment.

FIG. 11 is a block diagram showing the configuration of a pet medical checkup device 500 according to the present fifth embodiment.

The pet medical checkup device 500 of the fifth embodiment has the configuration substantially similar to that of the pet medical checkup device 100 of the first embodiment. The pet medical checkup device 500 of the fifth embodiment is different from the pet medical checkup device 100 of the first embodiment only in that a display section 13 is further provided. Accordingly, in the pet medical checkup device 500 of the fifth embodiment, constituent elements common to the pet medical checkup device 100 of the first embodiment are designated by the same reference numerals as those of the first embodiment. Hereinbelow, the configuration different from that of the first embodiment will be mainly described and the detailed description of the configuration common to the first embodiment will be omitted.

The display section 13 is used for reporting the estimation result of the estimation section 8 to the owner of the pet. The display section 13 may be, e.g., a mobile terminal having a display panel such as a so-called smartphone or tablet. The display section 13 may also be, e.g., a display device of a personal computer. The display section 13 may also be, e.g., a television set.

The estimation section 8 displays the estimation result of the disease of the pet in the display section 13. Only when it is determined that the pet has the disease (Yes in S9 of FIG. 4), the estimation section 8 may display the type of the disease of the pet in the display section 13. When it is not determined that the pet has the disease (No in S9 of FIG. 4), the estimation section 8 may display a message that the pet does not have the disease in the display section 13.

The estimation section 8 may display the image (a moving image or a still image) of the pet serving as an evidence for estimation of the disease in the display section 13 in addition to the estimation result of the disease of the pet. The estimation section 8 may display the shooting time of the image when the image of the pet serving as the evidence for the estimation of the disease is displayed in the display section 13. The estimation section 8 may display a plurality of the candidates for the disease in the display section 13 as the estimation result of the disease of the pet.

Figure 12:
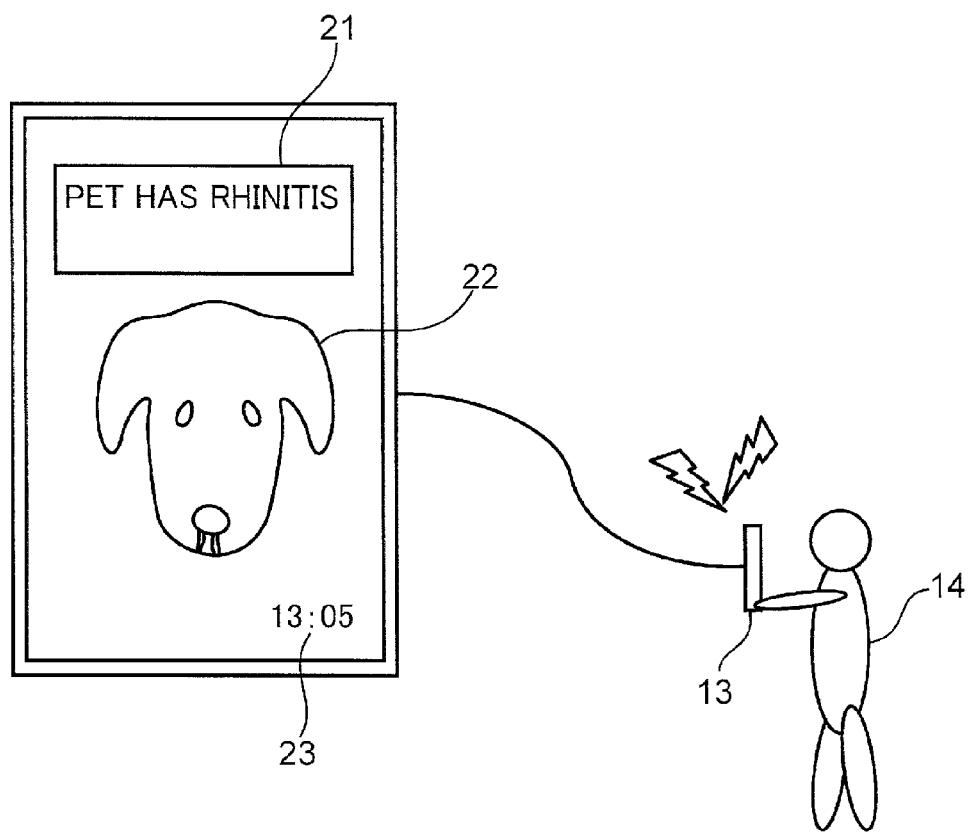
FIG. 12 is a view schematically showing an example of display of a display section according to the fifth embodiment.

FIG. 12 is a view schematically showing an example of the display of the display section 13. In FIG. 12, the display section 13 is a mobile terminal owned by an owner 14 of the pet. In the display section 13, an estimation result 21 of the disease of the pet is displayed in the form of a sentence "PET HAS RHINITIS". In addition, in the display section 13, a still image showing a running nose is displayed as an image 22 serving as the evidence for the estimation of the disease. In addition, in the display section 13, shooting time 23 at which the image 22 is shot is displayed.

As described thus far, in the pet medical checkup device 500 according to the fifth embodiment, the estimation section 8 displays the estimation result of the disease of the pet in the display section 13. Consequently, according to the fifth embodiment, the owner of the pet can know the disease of the pet quickly. As a result, the owner can take countermeasures such as taking the pet to a veterinary clinic immediately or the like.

Note that, in the fifth embodiment, the description has been given based on the configuration obtained by adding the display section 13 to the configuration of the first embodiment. Alternatively, the fifth embodiment may also have the configuration obtained by adding the display section 13 to the configuration of the second, third, or fourth embodiment.

In the case where the fifth embodiment has the configuration obtained by adding the display section 13 to the configuration of the third embodiment, the estimation section 8 may display a moving image with sound serving as the evidence for the estimation of the disease in the display section 13 in addition to the estimation result of the disease of the pet.

(Example of System Configuration)

Herein, a description will be given of an example of system configuration of each of the pet medical checkup devices 100 to 500 according to the first to fifth embodiments.

Figure 13:
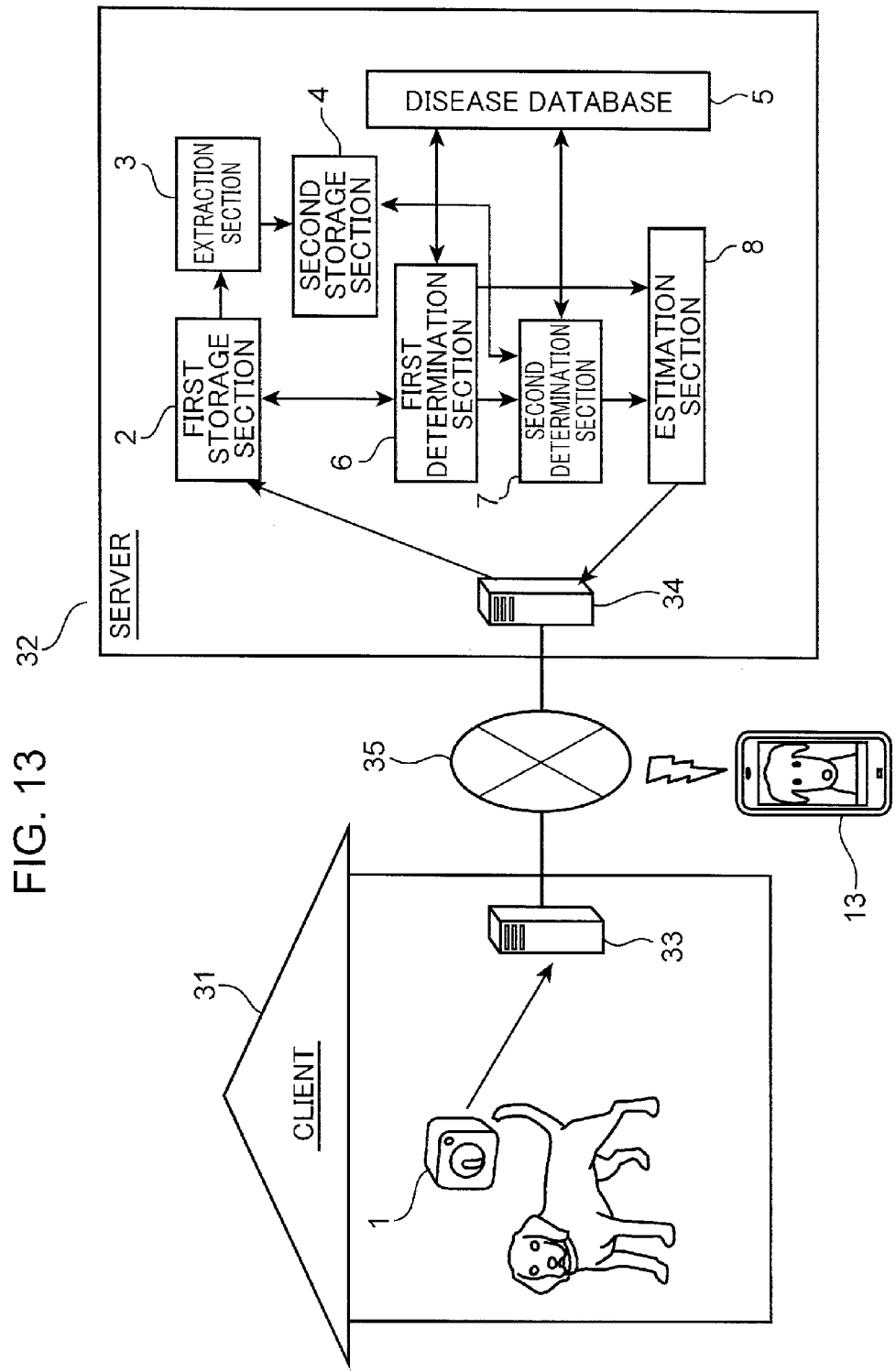
FIG. 13 is a view schematically showing an example of a system configuration of the pet medical checkup device according to the fifth embodiment.

FIG. 13 is a view schematically showing an example of the system configuration of the pet medical checkup device 500 according to the fifth embodiment.

The system shown in FIG. 13 includes a client 31 provided in a house and a server 32 provided outside the house. The client 31 includes a communication device 33. The server 32 includes a communication device 34. The client 31 and the server 32 are configured to be capable of communicating with each other using the communication devices 33 and 34 via a network 35.

Similarly to FIG. 12, the display section 13 of the pet medical checkup device 500 according to the fifth embodiment is a mobile terminal capable of communication via the network 35. The client 31 includes the shooting section 1 of the pet medical checkup device 500 according to the fifth embodiment. The server 32 includes the first storage section 2, the extraction section 3, the second storage section 4, the disease database 5, the first determination section 6, the second determination section 7, and the estimation section 8 of the pet medical checkup device 500 according to the fifth embodiment.

The shooting section 1 retains the shot moving image in the first storage section 2 via the communication device 33, the network 35, and the communication device 34. The estimation section 8 displays the estimation result of the disease of the pet in the display section 13 via the communication device 34 and the network 35. Note that, in FIG. 13, the first storage section 2 may be disposed in the client 31 instead of the server 32. In addition, in the case where the display section 13 is a television set, the display section 13 may be disposed in the client 31.

The pet medical checkup device 100 according to the first embodiment may have the system configuration similar to that of FIG. 13. That is, it is necessary to dispose the shooting section 1 in the client 31, but all of the other constituent elements may be disposed in the server 32. Alternatively, the shooting section 1 and the first storage section 2 may be disposed in the client 31. Further, alternatively, the shooting section 1, the first storage section 2, the extraction section 3, and the second storage section 4 may be disposed in the client 31.

The pet medical checkup device 200 according to the second embodiment may also have the system configuration similar to that of FIG. 13. That is, it is necessary to dispose the shooting section 1 in the client 31, but all of the other constituent elements may be disposed in the server 32. Alternatively, the shooting section 1 and the first storage section 2 may be disposed in the client 31. Further, alternatively, the shooting section 1, the first storage section 2, and the shooting control section 9 may be disposed in the client 31. Furthermore, alternatively, the shooting section 1 and the shooting control section 9 may be disposed in the client 31. In each of the alternative embodiments, the extraction section 3 and the second storage section 4 may be further disposed in the client 31.

The pet medical checkup device 300 according to the third embodiment may also have the system configuration similar to that of FIG. 13. That is, it is necessary to dispose the shooting section 1 and the sound collection section 10 in the client 31, but all of the other constituent elements may be disposed in the server 32. Alternatively, the first storage section 2 may be disposed in the client 31. Further, alternatively, the third storage section 11 may be disposed in the client 31.

The pet medical checkup device 400 according to the fourth embodiment may also have the system configuration similar to that of FIG. 13. That is, it is necessary to dispose the shooting section 1 in the client 31. In addition, in the case where the input section 12 is the mobile terminal, the input section 12 may be appropriately used also as the display section 13 shown in FIG. 13. Further, in the case where the input section 12 is the keyboard of the personal computer, the input section 12 may be appropriately disposed in the client 31. As described above, the first storage section 2 may be disposed in the client 31 or the server 32.

(Others)

In each of the embodiments, the constituent elements may be implemented by being constituted by dedicated hardware. The constituent elements may also be implemented by executing software programs appropriate for the constituent elements. The constituent elements may also be implemented by reading and executing software programs recorded in a recording medium such as a hard disk or a semiconductor memory using a program execution section such as a CPU or a processor.

Further, a part or all of the constituent elements constituting the individual devices may be constituted by a single system large scale integration (LSI). The system LSI is a super multifunctional LSI manufactured by integrating a plurality of elements on a single chip, and is specifically a computer system including a microprocessor, a ROM, and a RAM. In the ROM or the RAM, a computer program is stored. The microprocessor operates according to the computer program, and the system LSI thereby achieves its function.

Further, a part or all of the constituent elements constituting the individual devices may be constituted by an IC card that can be attached to or detached from each device or a stand-alone module. The IC card or the module is a computer system including the microprocessor, the ROM, and the RAM. The IC card or the module may include the super multifunctional LSI. The microprocessor operates according to the computer program, and the IC card or the module thereby achieves its function. The IC card or the module may have tamper resistance.

In addition, the present invention may be the methods described above. Further, the present invention may also be a computer program that implements these methods using a computer, or may also be a digital signal including the computer program.

Furthermore, the present invention may also be realized by recording the computer program or the digital signal in a computer-readable recording medium such as, e.g., a flexible disk, a hard disk, a CD-ROM, an MO, a DVD, a DVD-ROM, a DVD-RAM, a Blu-ray (registered trademark) Disc (BD), a USB memory, a memory card such as an SD card, or a semiconductor memory. Moreover, the present invention may also be the digital signal recorded in each of these recording media.

Additionally, the present invention may also be realized by the transmission of the computer program or the digital signal via a telecommunication line, a wired or wireless communication line, a network represented by the Internet, or data broadcasting.

In addition, the present invention may be a computer system including a microprocessor and a memory, the memory may store the computer program, and the microprocessor may operate according to the computer program.

Further, the devices may be implemented by an independent and different computer system by recording the program or the digital signal in the recording medium and transferring it or by transferring the program or the digital signal via the network or the like.

Furthermore, all of the numerals used in the above description are used for exemplification purpose for specifically describing the present invention, and therefore the present invention is not limited to the numerals exemplified.

Moreover, the division of the functional block in each block diagram is just an example. For example, a plurality of functional blocks may be implemented as a single functional block, the single functional block may be divided into the plurality of functional blocks, or a part of the function may be moved to another functional block. Additionally, the functions of a plurality of functional blocks having functions similar to one another may be processed by single hardware or software in parallel or in a time-sharing manner.

In addition, the order of execution of a plurality of steps included in the pet medical checkup method is an example for specifically describing the present invention, and an order other than the order may be employed. Further, a part of the steps may be executed simultaneously (in parallel) with another step.

Although the pet medical checkup devices according to one or a plurality of the aspects have been described based on the embodiments, the present invention is not limited to the embodiments. Other forms in which various modifications apparent to those skilled in the art are applied to the embodiments or forms structured by combining constituent elements of different embodiments may be included within the scope of one or a plurality of the aspects, unless such changes and modifications depart from the scope of the present invention.

The aspect of the present disclosure is useful as the pet medical checkup device capable of estimating the disease of the pet with excellent accuracy without giving stress to the pet.

This application is based on Japanese Patent application No. 2013-090087 filed in Japan Patent Office on Apr. 23, 2013, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A pet medical checkup device comprising:
   a shooting section that shoots a moving image of a subject pet;
   a first storage section that stores the moving image of the subject pet shot by the shooting section;
   an input section for inputting a type of pet;
   a first database that stores information indicating plural types of pets, information indicating types of diseases associated with each type of pet, and, for each type of pet and each type of disease associated therewith, motion information representing a characteristic motion made by the type of pet when the type of pet has the disease, respectively;
   a first determination section that determines whether or not the subject pet is making a characteristic motion of a disease corresponding to the type of pet inputted by the input section based on a comparison between the motion information stored in the first database and the moving image of the subject pet stored in the first storage section; and
   an estimation section that estimates the disease of the subject pet based on a determination result of the first determination section and provides an indication of the estimated disease.

2. The pet medical checkup device according to claim 1, further comprising:
   an extraction section that extracts a still image of the subject pet from the moving image of the subject pet stored in the first storage section;
   a second storage section that stores the still image of the subject pet extracted by the extraction section;
   a second database that stores image information representing a specific affected part image of an affected part related to the disease of the type of pet for each disease of the type of pet; and
   a second determination section that extracts a still image of the affected part related to the disease of the type of pet corresponding to the characteristic motion from the second storage section when the first determination section determines that the subject pet is making the characteristic motion, and determines whether or not the extracted still image includes the specific affected part image represented by the image information stored in the second database, wherein
   the estimation section estimates the disease of the subject pet based on the determination result of the first determination section and a determination result of the second determination section.

3. The pet medical checkup device according to claim 2, wherein
   the second database stores the image information for each type of pet, and
   the second determination section determines whether or not the still image of the affected part of the subject pet includes the specific affected part image correspondingly to the type of the pet inputted by the input section.

4. A pet medical checkup device comprising:
  a shooting section that shoots a moving image of a subject pet;
  a first storage section that stores the moving image of the subject pet shot by the shooting section;
  a first database that stores information indicating plural types of pets, information indicating types of diseases associated with each type of pet, and, for each type of pet and each type of disease associated therewith, motion information representing a characteristic motion made by the type of pet when the type of pet has the disease, respectively;
  a first determination section that determines whether or not the subject pet is making a characteristic motion of a disease corresponding to the kind of pet inputted by the input section based on a comparison between the motion information stored in the first database and the moving image of the subject pet stored in the first storage section; and
  an estimation section that estimates the disease of the subject pet based on a determination result of the first determination section and provides an indication of the estimated disease;
  a sound collection section that records a sound generated from the subject pet;
  a second storage section that stores the sound generated from the subject pet and recorded by the sound collection section; and
  a second database that stores motion sound information representing a sound generated by the characteristic motion made by the type of pet when the type of pet has the disease for each disease of the type of pet, wherein
  the first determination section determines whether or not the subject pet is making the characteristic motion represented by the motion information stored in the first database using the moving image of the subject pet stored in the first storage section and the motion sound information stored in the second storage section.

5. The pet medical checkup device according to claim 4, further comprising an input section for inputting a type of the pet, wherein
  the second database stores the motion sound information for each type of pet, and
  the first determination section determines whether or not the subject pet is making the characteristic motion corresponding to the type of pet inputted by the input section.

6. The pet medical checkup device according to claim 2, further comprising a shooting control section that changes a shooting condition of the shooting section, wherein
  the second determination section determines, before determining whether or not the still image extracted from the second storage section includes the specific affected part image, whether or not the still image is a determination-capable image that allows the determination, and, when determining that the still image is not the determination-capable image, the second determination section reports a detail of the determination that the still image is not the determination-capable image to the shooting control section, and
  the shooting control section changes the shooting condition of the shooting section based on the detail of the determination reported from the second determination section to thereby provide the still image as the determination-capable image.

7. The pet medical checkup device according to claim 1, wherein the estimation section causes a display section to display an estimation result.

8. A pet medical checkup method in a pet medical checkup device that estimates a disease of a subject pet, the method comprising:
  a shooting step of shooting a moving image of the subject pet;
  a storage step of causing a storage section to store the shot moving image of the subject pet;
  an input step of inputting a type of pet;
  a preparation step of preparing a database that stores information indicating plural types of pets, information indicating types of diseases associated with each type of pet, and, for each type of pet and each type of disease associated therewith, motion information representing a characteristic motion made by the type of pet when the type of pet has the disease, respectively;
  a determination step of determining whether or not the subject pet is making a characteristic motion of a disease corresponding to the type of the pet inputted in the input step based on a comparison between the motion information stored in the database and the moving image of the subject pet stored in the storage section; and
  an estimation step of estimating the disease of the subject pet based on a determination result in the determination step and providing an indication of the estimated disease.

9. A non-transitory computer readable recording medium recording a program for controlling a pet medical checkup device that estimates a disease of a subject pet, the program causing a computer of the pet medical checkup device to execute:
  a shooting step of shooting a moving image of the subject pet;
  a storage step of causing a storage section to store the shot moving image of the subject pet;
  an input step of inputting a type of pet;
  a preparation step of preparing a database that stores information indicating plural types of pets, information indicating types of diseases associated with each type of pet, and, for each type of pet and each type of disease associated therewith, motion information representing a characteristic motion made by the type of pet when the type of pet has the disease, respectively;
  a determination step of determining whether or not the subject pet is making a characteristic motion of a disease corresponding to the type of pet inputted in the input step based on a comparison between the motion information stored in the database and the moving image of the subject pet stored in the storage section; and
  an estimation step of estimating the disease of the subject pet based on a determination result in the determination step and providing an indication of the estimated disease.

* * * * *